(12) United States Patent
Civelli et al.

(10) Patent No.: US 9,012,407 B2
(45) Date of Patent: Apr. 21, 2015

(54) THERAPIES WHICH ACT ON NEUROPEPTIDE S RECEPTORS

(75) Inventors: Olivier Civelli, Irvine, CA (US); Rainer K. Reinscheid, Irvine, CA (US); Yanling Xu, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 1720 days.

(21) Appl. No.: 11/587,444

(22) PCT Filed: Apr. 25, 2005

(86) PCT No.: PCT/US2005/014312
§ 371 (c)(1),
(2), (4) Date: Sep. 9, 2009

(87) PCT Pub. No.: WO2005/110018
PCT Pub. Date: Nov. 24, 2005

(65) Prior Publication Data
US 2010/0056455 A1    Mar. 4, 2010

Related U.S. Application Data

(60) Provisional application No. 60/565,269, filed on Apr. 23, 2004.

(51) Int. Cl.
*A61K 38/17* (2006.01)
*A61K 31/4985* (2006.01)

(52) U.S. Cl.
CPC ......... *A61K 31/4985* (2013.01); *A61K 38/1709* (2013.01)

(58) Field of Classification Search
None
See application file for complete search history.

(56) References Cited

U.S. PATENT DOCUMENTS 5,902,797 A * 5/1999 Bell et al. .................. 514/54
7,323,541 B2 * 1/2008 Mori et al. ................. 530/300

FOREIGN PATENT DOCUMENTS

WO    WO 03025179 A1 *  3/2003

OTHER PUBLICATIONS

Garcia-Lopez et al. Antinociceptive effects in rodents of the dipeptide Lys-Trp (Nps) and related compounds. Peptides. 1986, vol. 7, No. 1, pp. 39-43.*
Xu et al. Neuropeptide S: A Neuropeptide Promoting Arousal and Anxiolytic-like Effects. Neuron. Aug. 19, 2004, vol. 43, pp. 487-497.*

* cited by examiner

*Primary Examiner* — Jeffrey E Russel
(74) *Attorney, Agent, or Firm* — Robert D. Buyan; Stout, Uxa & Buyan, LLP

(57) ABSTRACT

Compositions and methods that act on Neuropeptide S receptors (NPSR) (also known as "TGR23" or "vasopressin receptor-related receptor 1 (VRR1)") to cause desired effects in the bodies of human or animal subjects. Neuropeptide S (NPS) and other agonists of the NPSR may be administered to cause arousal, awakening, alertness, spontaneous movement, bronchoconstriction, contraction of bronchial smooth muscle or other effects. Antagonists of the NPSR may be administered to cause decreased arousal, decreased awakening, decreased alertness, decreased spontaneous movement, sleep, somnolence, sedation, anxiolytic effects, normalized sleep patterns, normalized sleep stages, increased duration of sleep, bronchodilation, relaxation of broncheal smooth muscle or other effects.

3 Claims, 14 Drawing Sheets

| | | |
|---|---|---|
| (SEQ ID NO: 1) | SFRNGVGTGMKKTSFQRAKS | human |
| (SEQ ID NO: 2) | SFRNGVGTGMKKTSFRRAKS | chimpanzee |
| (SEQ ID NO: 3) | SFRNGVGSGAKKTSFRRAKQ | mouse |
| (SEQ ID NO: 4) | SFRNGVGSGVKKTSFRRAKQ | rat |
| (SEQ ID NO: 5) | SFRNGVGTGMKKTSFRRAKS | dog |
| (SEQ ID NO: 6) | SFRNGVGSGIKKTSFRRAKS | chicken |

Figure 1

Open Field

Light-Dark Box

Elevated Plus Maze

Marble Burying

Table 1: EC$_{50}$ values (nM, ± SEM) of NPS peptides and NPS fragments at two NPSR isoforms

| Peptide | Sequence | | NPSR WT | NPSR Ile$^{107}$ |
|---|---|---|---|---|
| hNPS 1-20 | SFRNGVGTGMKKTSFQRAKS | (SEQ ID NO: 1) | 8.43 ± 1.47 | 1.78 ± 1.31 |
| hNPS 1-18 | SFRNGVGTGMKKTSFQRA | (SEQ ID NO: 7) | 10.9 ± 1.2 | 2.59 ± 1.45 |
| rNPS 1-20 | SFRNGVGSGVKKTSFRRAKQ | (SEQ ID NO: 4) | 3.1 ± 1.34 | 0.86 ± 0.13 |
| mNPS 1-20 | SFRNGVGSGAKKTSFRRAKQ | (SEQ ID NO: 3) | 2.8 ± 1.37 | 0.77 ± 0.14 |
| hNPS 1-12 | SFRNGVGTGMKK | (SEQ ID NO: 8) | > 10.000 | 2520 ± 118 |
| rNPS 1-10 | SFRNGVGSGV | (SEQ ID NO: 9) | 2090 ± 238 | 18.8 ± 13.6 |
| hNPS 4-20 | NGVGTGMKKTSFQRAKS | (SEQ ID NO: 10) | inactive | inactive |

All peptides were tested for mobilization of intracellular Ca$^{2+}$ in two independent stable clones expressing the respective NPSR isoform. EC$_{50}$ values were calculated from triplicate incubations. Data from a typical experiment are shown. The human NPS 1-10 peptide was insoluble and could not be tested; h, human; m, mouse; r, rat.

Figure 9

THERAPIES WHICH ACT ON NEUROPEPTIDE S RECEPTORS

RELATED APPLICATION

This application is a Section 371 national stage of PCT International Patent Application No. PCT/US05/14312 filed Apr. 25, 2005 which claims priority to U.S. Provisional Patent Application No. 60/565,269 filed on Apr. 23, 2004, the entirety of which is expressly incorporated herein by reference.

STATEMENT REGARDING GOVERNMENT SUPPORT

This invention was made with Government support under Grant Nos. MH-60231 awarded by the National Institutes of Health. The Government has certain rights in this invention.

SEQUENCE LISTING

The instant application contains a Sequence Listing which has been submitted electronically in ASCII format and is hereby incorporated by reference in its entirety. Said ASCII copy, created on Dec. 15, 2014, is named UCIVN-064US SL-FILED.txt and is 6,395 bytes in size.

FIELD OF THE INVENTION

The present invention relates generally to the fields of biology and medicine, and more particularly to compositions and methods for affecting neuropeptide S (NPS) receptors to treat various disorders, including but not limited to narcolepsy, insomnia, drowsiness, hypersomnia, anxiety, asthma and allergies.

BACKGROUND OF THE INVENTION

As described in United States Provisional Patent Application No. 60/565,269, an endogenous brain protein, Neuropeptide S (NPS) which is believed to affect arousal, wakefulness, propensity for movement, asthma and some allergic responses, stress associated with several anxiety disorders and other physiological functions. Human NPS (hNPS) has the following amino acid sequence: Ser-Phe-Arg-Asn-Gly-Val-Gly-Thr-Gly-Met-Lys-Lys-Thr-Ser-Phe-Gln-Arg-Ala-Lys-Ser-OH (SEQ ID NO:1). It is now available commercially as product No. E010051 from PentaBiotech, Inc., Union City, Calif.

Neuropeptide S is the endogenous ligand for the Neuropeptide S receptor (NPSR), which has also been referred to as TGR23 and vasopressin receptor-related receptor 1 (VRR1) (Genbank accession no. BD183774, BD183814, BD183773). The NPSR is a G protein coupled receptor (GPCR).

NPS acts as an agonist of the NPSR, causing dose dependent intracellular Ca++ mobilization as well as adenyl cyclase accumulation measured by cAMP assay. NPS is also involved in G protein-coupled receptor for asthma susceptibility. Y. L. Xu, R. X. Reinscheid, S. Huitron-Resendiz, S. D. Clark, Z. Wang, S. H. Lin, F. A. Brucher, J. Zeng, N. K. Ly, S. J. Henriksen, L. d'Lecea, O. Civelli, Neuron, 43, 487-497 (2004).

PCT International Patent Publication WO 02/31145 A1 (Sato) describes certain functions of NPS and the NPSR. However, PCT International Patent Publication WO 02/31145 A1 (Sato) does not describe specific pharmacological characteristics and physiological functions of the GPCR system, NPS, the NPSR or its amino acid sequence (Genbank accession no. BD183774, BD183814, BD183773). PCT International Patent Publication WO 02/31145 A1 (Sato) is expressly incorporated herein in its entirety.

PCT International Patent Publication WO 2005/021555 A1 (Takeda Pharmaceutical Company) described certain bicyclic piperazine compounds that a NPSR antognists and are purportedly useable in the prevention and treatment of certain cancers. PCT International Patent Publication WO 2005/021555 A1 (Takeda Pharmaceutical Company) is expressly incorporated herein by reference.

Definitions

When used in this patent application, the following terms and abbreviations shall be interpreted as follows:

The verb "to treat" and formatives/tenses thereof (i.e., treats, treating, treatment, etc.) shall include therapeutic, preventative, paliative, experimental and diagnostic treatments.

The term "subject" shall include human and other animal patients and non-patient subjects who receive therapeutic, preventative, experimental or diagnostic treatment, humans and animals who have a disease or are predisposed to a disease and/or laboratory animals or humans who on whom tests or experiments are performed.

Compositions or methods "comprising" one or more recited elements may include other elements not specifically recited. For example, a composition that comprises NPS may encompass both an isolated NPS of human or animal origin as a component of a larger polypeptide sequence or as part of a composition or preparation that includes other pharmacologically active or inactive ingredients or components.

The term "Isolated" means purified, substantially purified or partially purified. Isolated can also mean present in an environment other than a naturally occurring environment. For example, NPS that is not present in or mixed with nervous tissue, extracellular fluid, cerebrospinal fluid of other body fluids/tissues in which NPS would ordinarily be found when naturally occurring shall be deemed to be isolated NPS.

The verb "to administer" and formatives/tenses thereof (i.e., administers, administering, administration, etc.) shall include any act of providing or delivering a substance to a human or animal subject or to in vitro preparation, including but not limited to oral, enteral, intravenous, intraarterial, parenteral, subcutaneous, intradermal, transdermal, transmucosal, buccal, sublingual, lingual, rectal, intraperitoneal, central, intraventricular, intrathecal, epidural, spinal, topical, alveolar, inhalational, transtracheal and all other routes by which such substance may be administered or provided. Additionally, acts that cause, induce, stimulate, accelerate, enhance or facilitate the biosynthesis or endogenous production of an endogenous naturally occurring substance (e.g., endogenous NPS) shall also be construed as acts of "administering" such substance. Additionally, acts that inhibit, decrease, slow, interfere with or block the metabolism and/or clearance of a naturally occurring substance (e.g., endogenous NPS) so as to result in the presence of increased or greater amounts of the substance within the body of a human or animal subject shall also be construed as acts of "administering" such substance.

The acronym "NPS" shall mean "neuropeptide S", including those of human and animal origin having the amino acid sequences shown in FIG. 1.

The acronym "hNPS" shall mean "human neuroeptide S", the amino acid sequence of which is: Ser-Phe-Arg-Asn-Gly-Val-Gly-Thr-Gly-Met-Lys-Lys-Thr-Ser-Phe-Gln-Arg-Ala-Lys-Ser-OH (SEQ ID NO: 1).

The acronym "NPSR" shall mean "neuropeptide S receptor" or "TGR23" or "vasopressin receptor-related receptor 1."

The acronym "WT" shall mean "wildtype."

The acronym "GPCR" shall mean "G protein-coupled receptor."

The acronym "SNP" shall mean "single nucleotide polymorphism."

The acronym "MAPK" shall mean "mitogen-activated protein kinase."

The acronym "LC" shall mean "locus coeruleus."

The acronym "Ala" or the symbol "A" shall mean "Alanine."

The acronym "Arg" or the symbol "R" shall mean "Arginine."

The acronym "Asn" or the symbol "N" shall mean "Asparagine."

The acronym "Asp" or the symbol "D" shall mean "Aspartic Acid."

The acronym "Asx" or the symbol "B" shall mean "Asparagine or Aspartic Acid."

The acronym "Cys" or the symbol "C" shall mean "Cystine."

The acronym "Gln" or the symbol "Q" shall mean "Glutamine."

The acronym "Glu" or the symbol "E" shall mean "Glutamic Acid."

The acronym "Glx" or the symbol "Z" shall mean "Glutamine or Glutamic Acid."

The acronym "Gly" or the symbol "G" shall mean "Glycine."

The acronym "His" or the symbol "H" shall mean "Histidine."

The acronym "Ile" or the symbol "I" shall mean "Isoleucine."

The acronym "Leu" or the symbol "L" shall mean "Leucine."

The acronym "Lys" or the symbol "K" shall mean "Lysine."

The acronym "Met" or the symbol "M" shall mean "Methionine."

The acronym "Phe" or the symbol "F" shall mean "Phenylalanine."

The acronym "Pro" or the symbol "P" shall mean "Proline."

The acronym "Ser" or the symbol "S" shall mean "Serine."

The acronym "Thr" or the symbol "T" shall mean "Threonine."

The acronym "Trp" or the symbol "W" shall mean "Tryptophan."

The acronym "Tyr" or the symbol "Y" shall mean "Tyrosine."

The acronym "Val" or the symbol "V" shall mean "Valine."Additional terms, acronyms and/or symbols are defined elsewhere in this patent application.

SUMMARY OF THE INVENTION

The present invention provides a composition of matter comprising isolated NPS.

Further in accordance with the present invention, NPSR agonists may be administered to human or veterinary subjects in effective dosages and by effective routes of administration to cause arousal, awakening, alertness, anxiolytic effects, spontaneous movement or to induce bronchoconstriction, bronchial smooth muscle contraction or asthma (e.g., for diagnostic or experimental purposes) and/or other effects as described herein. Thus, NPS agonists may be useable to treat disorders such as; narcolepsy, hypersomnia, lack of alertness, lack of attentiveness, absentmindedness, lack of or aversion to movement or exercise, anxiety, stress and stress related disorders, and other disorders as described herein. Examples of NPSR agonists that may be administered in accordance with this invention include but are not necessarily limited to NPS, isolated NPS, fragments of NPS, compositions that comprise NPS or other agonists of the NPSR.

Still further in accordance with the present invention, NPSR antagonists and preparations that comprise NPSR antagonists may be administered to human or veterinary subjects in effective dosages and by effective routes of administration to cause; decreased arousal, decreased awakening, decreased alertness, decreased spontaneous movement, sleep, somnolence, sedation, normalized sleep patterns, normalized sleep stages, increased duration of sleep, bronchodilation, relaxation of broncheal smooth muscle and/or other effects as described herein. Thus, NPSR antagonists (e.g., compounds of General Formula I above) and preparations that comprise NPSR antagonists may useable to treat disorders such as insomnia, sleep disorders, decreased duration of sleep or frequent awakening, disorders that cause excessive spontaneous movement, some behavioral disorders, bronchitis, obstructive pulmonary disease, asthma, allergic conditions and other disorders as described herein. Examples of NPSR antogonists that may be administered in accordance with this invention include but are not necessarily limited to those of General Formula I, as follows:

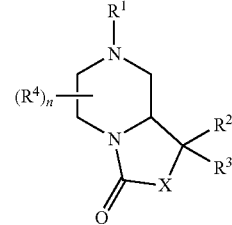

wherein $R^1$ comprises acyl; $R^2$ comprises an optionally substituted hydrocarbon group; $R^3$ comprises an optionally substituted hydrocarbon group; $R^4$ comprises an optionally substituted hydrocarbon group; n is 0 to 4; and X comprises oxygen, sulfur, etc.) or a salt of such compound.

Still further aspects and objects of the present invention may be understood from the detailed description and examples set forth herebelow.

BRIEF DESCRIPTION OF THE DRAWINGS

FIG. 1 shows primary structures of NPS from human, chimpanzee, rat, mouse, dog and chicken. Amino acids divergent from the human sequence are shown in bold type. Sequences were deduced from Genbank entries BD168686 (human), BD168712 (rat), BD168690 (mouse), BU293859 (chicken), and genome sequencing traces 231487919 (chimpanzee) and 250468833 (dog).

FIG. 2A is a dose response curve of $[Ca^{2+}]i$ mobilization induced by human, rat and mouse NPS in an HEK cell line stably expressing human NPSR. FIG. 2B shows saturation binding of $[^{125}I]$ $Y^{10}$-NPS (4 pM-1.7 nM) to CHO cells stably expressing human NPSR.

FIG. 2C shows displacement of 0.15 nM [$^{125}$I] Y$^{10}$-NPS by increasing concentrations of unlabeled human NPS. Data from triplicate experiments are shown as means±SEM.

FIG. 4A is a schematic drawing of a cross section of the pontine area of the rat brain. FIG. 4B is an autoradiogram of NPS mRNA expression in LC area. FIGS. 4C-4E are dark field images of double in situ hybridization of NPS precursor mRNA (white) and TH mRNA (dark blue) in LC area. FIG. 4D is a higher magnification view of area 4D-4D of FIG. 4C. FIG. 4E is a higher magnification view of a more caudal section. FIGS. 4F-4H are dark field images of double in situ hybridization of NPS precursor mRNA (white) and CRF mRNA (dark blue) at mid-level of LC area (F) and rostral LC (G). (H) Higher magnification of the area indicated by an arrow in (G). TH, tyrosine hydroxylase; NPS, neuropeptide S; CRF, corticotropin-releasing factor; Landmarks: Cb, cerebellum; 4V, 4th ventricle. Scale bar is 500 μm in (C), 250 μm in all other pictures.

FIGS. 5A, 5D and 5G are drawings and FIGS. 4B, 4C, 4E, 4F, 4H and 4I are autoradiograms of sections of the rat brains. (4B and 4C-(Bregma −9.68 mm), (4E and 4F-Bregma −2.80 mm) and (4H and 4I-Bregma −3.14 mm), respectively (Paxinos and Watson, 1997). (B), (C), (E), (F), (H), (I) Darkfield images of NPS precursor mRNA expression in coronal sections of rat brain. (E), (H) Expression of NPS precursor mRNA in boxed regions in (D) and (G), respectively. (C), (F), (I) Higher magnification of the area indicated by an arrow in (B), (E) and (H), respectively. Arrows in (F) and (I) indicate single cells showing hybridization signals for NPS precursor mRNA. LPB, lateral parabrachial nucleus; Pr5, principle sensory 5 nucleus; DMH, dorsomedial hypothalamic nucleus; Amg, amygdala. Landmarks: Cb, cerebellum; 3V, third ventricle; opt, optic tract. Scale bar is 500 μm.

FIG. 9 is a table showing $EC_{50}$ values (nM, +/− SEM) of NPS peptides and NPS fragments at two NPSR isoforms.

DETAILED DESCRIPTION AND EXAMPLES

Figure 2A:
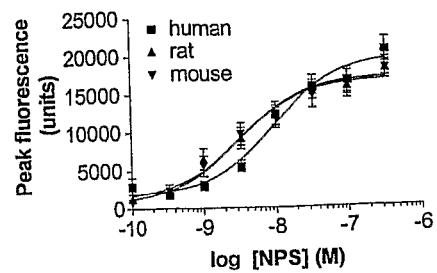
FIGS. 2A-2C are graphs showing pharmacological characterization of the human NPSR.

The amino acid sequences of NPS in humans, chimpanzees, mice, rats, dogs and chickens are shown in FIG. 1. The NPSR is expressed in certain regions of the brain known to be involved in anxiety (e.g., the amygdala, thalamus and hypothalamic regions). Administration of NPS to rodents can cause increased locomotion and anxiolytic effects. Also, Applicants have determined that NPS plays a roll in asthma (e.g., constriction and/or dilation of bronchi and/or contraction/relaxation of bronchiolar smooth muscle).

Arousal and anxiety are behavioral responses that involve complex neurocircuitries and multiple neurochemical components. As described herein, NPS may be useable to modulate wakefulness and could also regulate anxiety. NPS acts by activating its cognate receptor (NPSR) and inducing mobilization of intracellular $Ca^{2+}$. The NPSR mRNA is widely distributed in the brain including the amygdala and the midline thalamic nuclei. Central administration of NPS increases locomotor activity in mice and decreases paradoxical (REM) sleep and slow wave sleep in rats. NPS was further shown to produce anxiolytic-like effects in mice exposed to four different stressful paradigms. Interestingly, NPS is expressed in a previously undefined cluster of cells located between the LC and Barrington's nucleus. These results indicate that NPS could be a new modulator of arousal and anxiety. They also show that the LC region encompasses distinct nuclei expressing different arousal-promoting neurotransmitters.

Sleep disorders and anxiety affect millions of people. Identifying and understanding the molecular regulators and neurocircuitries that are involved in sleep/wake cycles or arousal and anxious states are keys to the development of therapeutic targets for these diseases. Neurochemically, it has been shown that classical neurotransmitters such as noradrenaline (NA) (Aston-Jones et al., 1991a; Berridge and Waterhouse, 2003), acetylcholine (Jones, 1991; Millan, 2003), serotonin (Millan, 2003; Ursin, 2002), glutamate (Chojnacka-Wojcik et al., 2001; Jones, 2003) and GABA (Gottesmann, 2002) are important transmitters of arousal systems and also play important roles in regulating emotional states as they relate to anxiety-like behavior. In addition, various neuropeptides such as hypocretin/orexin(Hcr/Ox) (Sutcliffe and de Lecea, 2002), neuropeptide Y (Silva et al., 2002), galanin (Bing et al., 1993; Holmes et al., 2003; Saper et al., 2001), or nociceptin/orphanin FQ (Reinscheid and Civelli, 2002) are also modulators of arousal and/or anxiety. Anatomically, the dorsolateral pontine tegmental region is one of the important areas that have been implicated in both sleep regulation and stress-related behaviors. The dorsolateral tegmental region contains several distinct nuclei such as Barrington's nucleus, the locus coeruleus (LC) and also comprises unidentified neurons outside of the LC proper such as the peri-LC region (Rizvi et al., 1994; Sutin and Jacobowitz, 1988). The LC is the primary source of noradrenergic input to the cortex and the NA-LC system plays important roles in regulating arousal and anxiety (Berridge and Waterhouse, 2003; Swanson and Hartman, 1975). Firing of LC neurons correlates with vigilance states. Tonic discharge of LC neurons is virtually absent during rapid eye movement (REM) sleep, low during slow wave sleep (SWS stages 1 and 2) and highest during wakefulness (Foote et al., 1980; Hobson et al., 1975). Barrington's nucleus, the pontine micturition reflex center, expresses corticotrophin-releasing factor (CRF) as its peptidergic neurotransmitter (Sutin and Jacobowitz, 1988; Swanson et al., 1983; Valentino et al., 1995).

In addition to these known neurotransmitters and neurocircuities that are involved in arousal and anxiety, there could be other important regulators and structures in the CNS that have not yet been uncovered. Novel neurotransmitters or modulators can be found by using orphan G protein-coupled receptors (GPCRs) as targets. Orphan GPCRs are cloned receptor proteins whose endogenous ligands have not yet been identified. Identification of the natural ligands (deorphanization) of orphan GPCRs leads to the discovery of novel neurotransmitters or modulators. Using orphan GPCRs several novel neuropeptides have recently been discovered which ultimately have shed new insights on our understanding of particular brain functions and helped to reveal novel therapeutic targets for mental disorders.

Described herein are certain physiological functions of such a newly deorphanized GPCR system, NPS, and its cognate GPCR. The sequence of the GPCR (Genbank accession no. BD183774, BD183814, BD183773) was first disclosed in a patent published in April 2002 ((WO 02/31145 A1) (Sato, 2002). The patent also reported the isolation of its endogenous peptide ligand without providing further information about pharmacological characteristics and physiological functions. Here, we report that NPS is a novel neuropeptide that potently modulates arousal and could also regulate anxiety-related behavior. We further analyze the distribution of the NPS precursor mRNA expression and describe the existence of a previously uncharacterized population of cells that are adjacent to the noradrenergic LC neurons.

Evolutionary Conservation of NPS Primary Structures

The human, rat and mouse NPS precursor proteins contain a hydrophobic signal peptide and a pair of basic amino acid residues preceding the unprocessed peptide. Searching public DNA databases we identified a chicken EST clone and partial genomic sequences for the chimpanzee and canine precursor proteins. Alignment of the deduced primary structures of the mature peptide shows that the amino-terminal residue in all species is a conserved serine (FIG. 1). According to the nomenclature that has been used most recently (Shimomura et al., 2002), we propose to term this novel peptide "Neuropeptide S" (NPS).

Pharmacological Profiles of NPS and NPSR

Cell lines stably expressing human NPSR in both Chinese hamster ovary (CHO) cells and human embryonic kidney 293 T cells (HEK 293T) were used to define the pharmacological characteristics of NPS. Human, rat and mouse NPS induce dose dependent elevations in intracellular $[Ca^{2+}]_i$, in both HEK 293T (FIG. 2A) and CHO (data not shown) cell lines, indicating that the NPSR couples to $G_q$ proteins. Half-maximal effective concentrations $(EC_{50})$ for mobilization of $[Ca^{2+}]_i$, were 9.4±3.2 nM, 3.2±1.1 nM and 3.0±1.3 nM for human, rat and mouse NPS, respectively.

Since position 10 of NPS is not conserved among the different species we decided to substitute the corresponding amino acid by tyrosine (Y) in order to develop an analog suitable for radioiodination. Human $Y^{10}$-NPS retains full agonist activity with an $EC_{50}$ of 6.7±2.4 nM (data not shown).

Figure 2B:
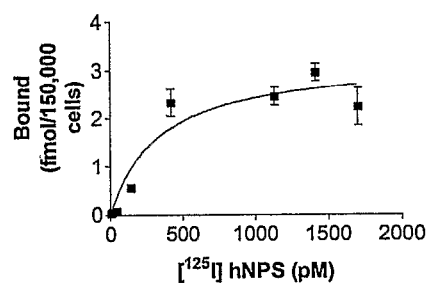
Figure 2C:
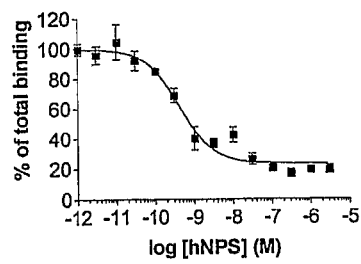

The monoiodinated form of $Y^{10}$-NPS was used as a radioligand in receptor binding experiments. Binding of [125I] $Y^{10}$-hNPS to CHO cells stably expressing hNPSR is saturable with high affinity ($K_d$=0.33±0.12 nM; $B_{max}$=3.2±0.4 fmol/150.000 cells, FIG. 2B) and displaceable by increasing concentrations of human NPS ($IC_{50}$=0.42±0.12 nM) (FIG. 2C). No specific binding was detected in mock-transfected CHO cells. These results demonstrate that NPS binds and activates its cognate receptor with high potency and specificity.

Distribution of NPS Precursor and Receptor mRNA Expression

Figure 3A:
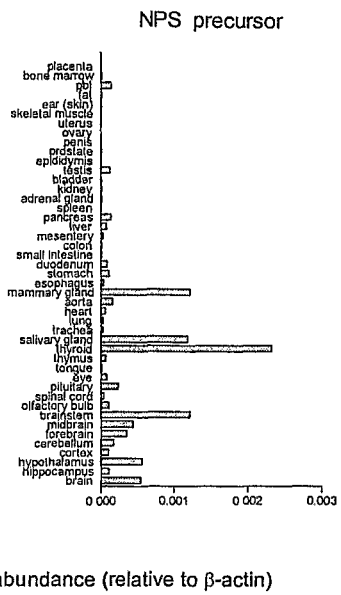
FIG. 3A and 3B are bar graphs showing tissue distribution of NPS precursor (FIG. 3A) and NPSR mRNA (FIG. 3B) in rat tissues. Quantitative RT-PCR was used to measure transcript levels of NPS precursor (left) and NPSR mRNA (right) in 45 rat tissues. Transcript levels were normalized to β-actin. pbl, peripheral blood leucocytes.
Figure 3B:
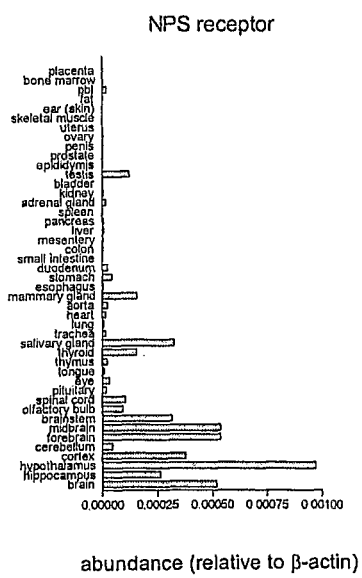

We next examined the sites of synthesis of the NPS precursor and receptor mRNA in rats. Quantitative RT-PCR shows that NPS and its receptor are expressed in various tissues, the highest levels being found in brain, thyroid, salivary and mammary glands (FIG. 3).

Figure 4A:
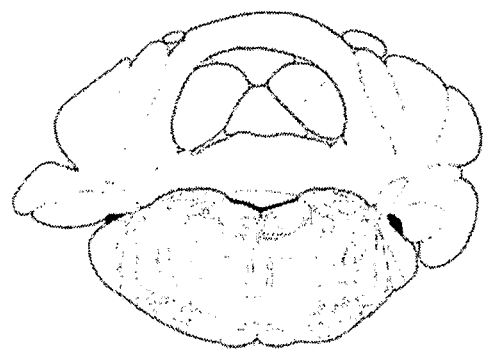
FIGS. 4A-4H show expression of NPS precursor mRNA in the pontine area of the rat brain.
Figure 4B:
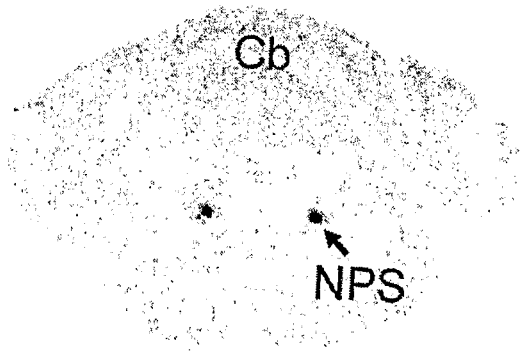
Figure 5A:
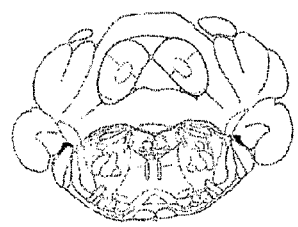
FIGS. 5A-5I show the distribution of NPS precursor mRNA expression in rat brain.
Figure 5B:
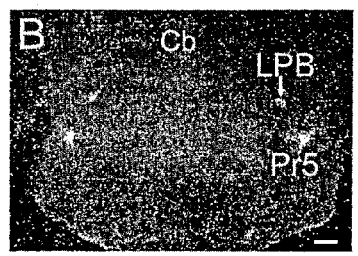
Figure 5C:
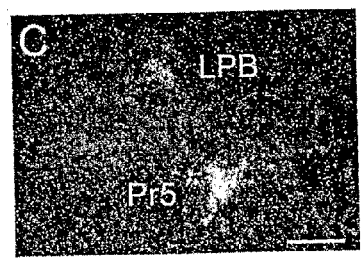
Figure 5D:
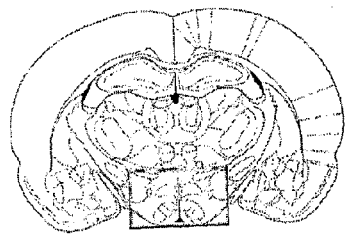
Figure 5E:
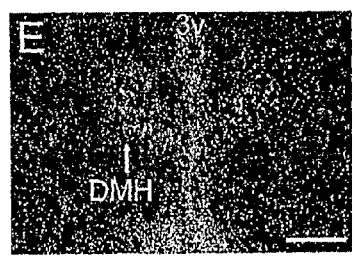
Figure 5F:
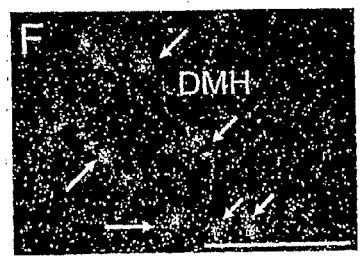
Figure 5G:
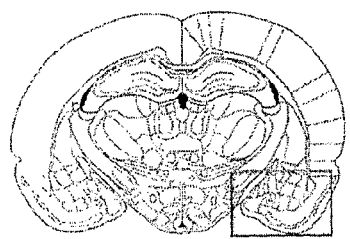
Figure 5H:
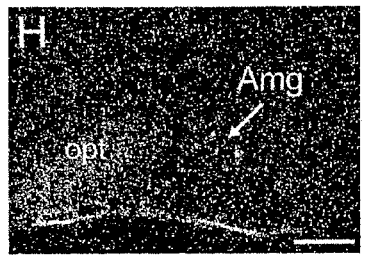
Figure 5I:
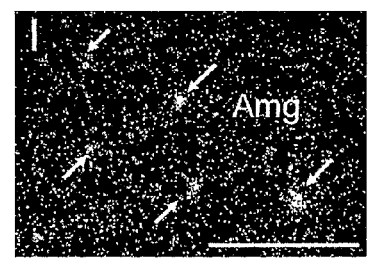

Since both NPS and NPSR mRNA are expressed highly in CNS among all the tissues examined, we next studied the localization of NPS and its receptor mRNA in rat brains by in situ hybridization. These experiments revealed that the rat NPS precursor mRNA is expressed discretely in a few brain areas, with strongest expression in the LC area (FIG. 4B), principle sensory 5 nucleus and lateral parabrachial nucleus (FIG. 5B, C). Moderate expression was also found in a few scattered cells of the dorsomedial hypothalamic nucleus (FIG. 5E, F) and the amygdala (FIG. 5H, I).

Figure 4C:
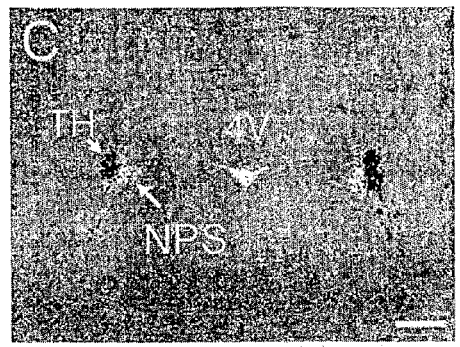
Figure 4D:
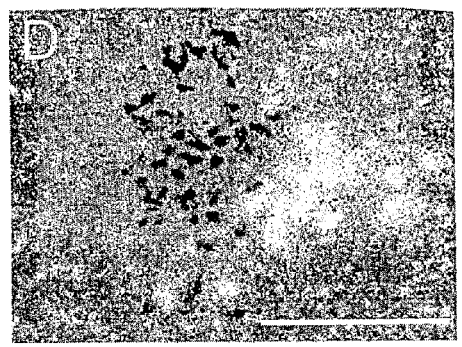
Figure 4E:
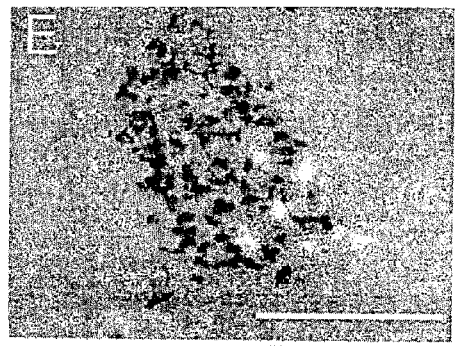

To describe the NPS expressing neurons in the LC area more precisely, double in situ hybridization with antisense probes for NPS precursor and tyrosine hydroxylase (TH) was carried out. As shown in FIG. 4C-E, NPS does not colocalize with TH. The majority of NPS positive cells were observed at midpontine levels, ventromedial to the noradrenergic LC neurons. Few NPS expressing neurons were found intermingled with TH positive cells at the ventral pole of LC proper. We conclude that the NPS expressing neurons in the LC area form a cluster of cells that do not produce NA and intermingle with LC proper neurons along the medial and ventral border of LC, extending just medially into the peri-LC area.

Figure 4F:
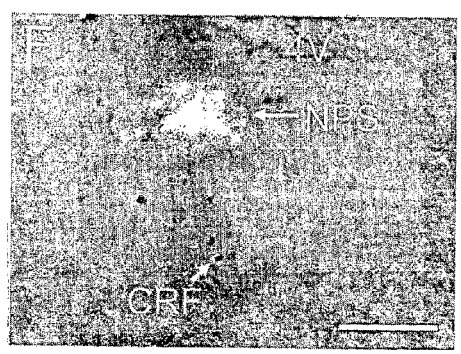
Figure 4G:
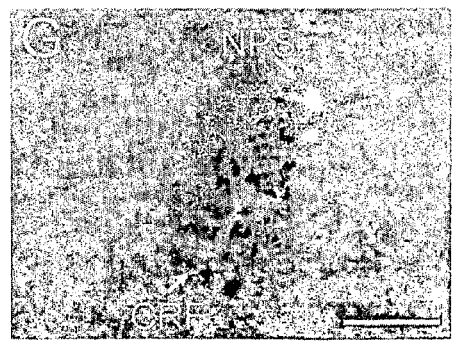
Figure 4H:
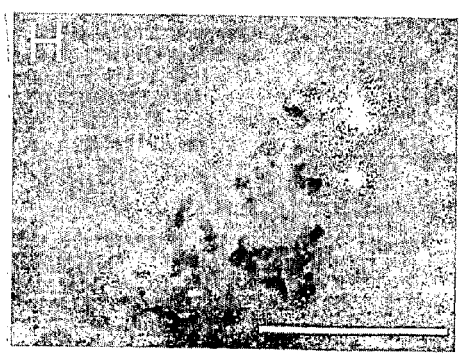

Within that area and ventromedial to the LC lies Barrington's nucleus, the micturition reflex center, which is a well-studied ovoid shaped nucleus located at the rostral pole of LC. It has been shown that Barrington's nucleus is negative for TH and choline acetyltransferase and most of its neurons express CRF (Rizvi et al., 1994; Valentino et al., 2000). Double in situ hybridization with NPS and CRF antisense riboprobes revealed that NPS does not colocalize with CRF (FIG. 4F-H). At the level of highest NPS neuron density, only a few scattered neurons were found expressing CRF that were located ventrally to the NPS expressing neurons. At a more rostral level, densely packed CRF positive neurons were observed as the ovoid shaped Barrington's nucleus. Only few NPS expressing neurons were found along the dorsal border of Barrington's nucleus at this level. We conclude that the NPS expressing neurons lie caudally to Barrington's nucleus and at the mid-level of LC. They extend ventromedially from the LC proper, caudodorsally to Barrington's nucleus. This unique anatomical pattern of NPS expressing neurons defines a previously unrecognized population of cells located in between the noradrenergic LC proper and Barrington's nucleus.

Figure 6A:
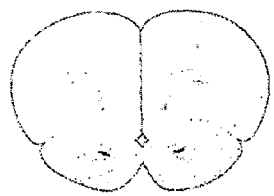
FIGS. 6A-6O show the distribution of NPSR mRNA expression in rat brain. (A), (D), (G), (J) Schematic drawings of the sections shown in (B) and (C) (Bregma, 3.20 mm), (E) and (F) (Bregma −1.80 mm), (H) and (I) (Bregma −2.80 mm), (K) and (L) (Bregma −4.52 mm), respectively (Paxinos and Watson, 1997). (B), (E), (H), (K) Autoradiograms of NPSR mRNA expression in coronal rat brain sections. Arrows in panel (B), (E), (H) and (K) indicate endopiriform nucleus (En). Arrowheads in (E), (H) and (K) refer to secondary motor cortex (M2), retrosplenial agranular cortex (RSA)/M2 and RSA, respectively. (C), (F), (I) Dark field images of boxed regions in (B), (E) and (H), respectively. (L) Dark field image of midline thalamic regions of section (K). (M), (N) Dark field image of cortical regions in section (E). Arrows in (N) indicate scattered cells expressing NPSR mRNA in somatosensory cortex. (O) Dark field image of cortical and subicular regions in section (K). AON, anterior olfactory nucleus; DEn: dorsal endopiriform nucleus, CM, central medial thalamic nucleus; IAM, interanteromedial thalamic nucleus, Rh, rhomboid thalamic nucleus; Re, reuniens thalamic nucleus; Amg, amygdala; Hyp, hypothalamus; S, subiculum; Prc, precommissural nucleus; PVP, paraventricular thalamus nucleus, posterior; PH, posterior hypothalamus. Landmarks: aca, anterior commissure, anterior part; pt, paratenial thalamic nuclei; opt, optic tract; D3V, dorsal 3rd ventricle; 3V, 3rd ventricle; Hip, hippocampus. Scale bar is 500 μm.
Figure 6B:
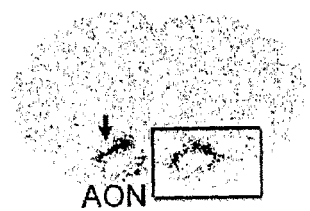
Figure 6C:
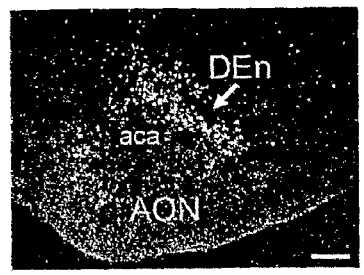
Figure 6D:
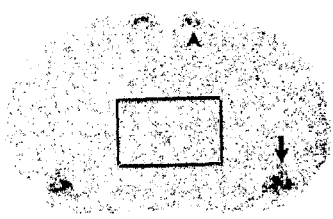
Figure 6E:
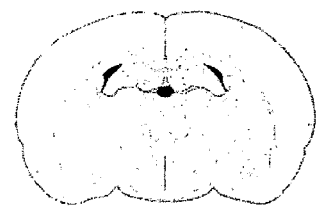
Figure 6F:
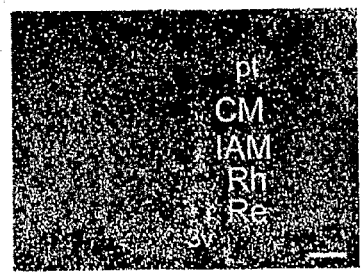
Figure 6G:
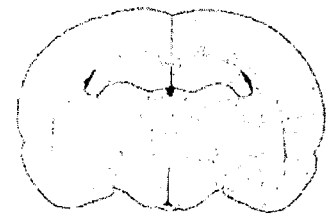
Figure 6H:
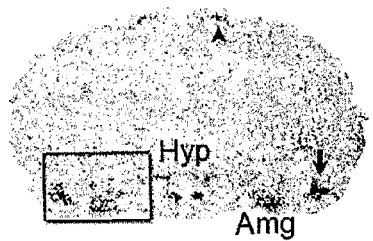
Figure 6I:
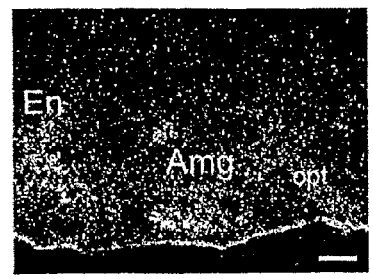
Figure 6J:
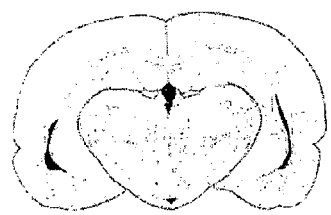
Figure 6K:
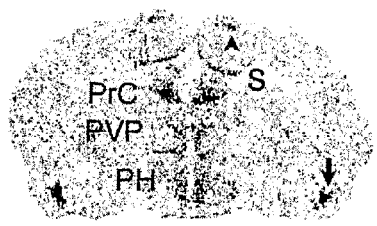
Figure 6L:
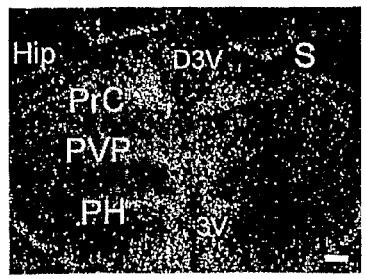
Figure 6M:
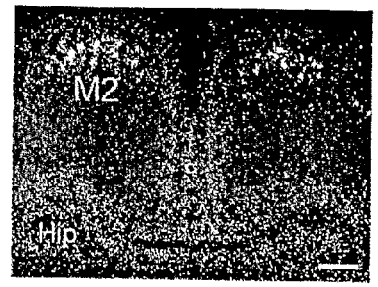
Figure 6N:
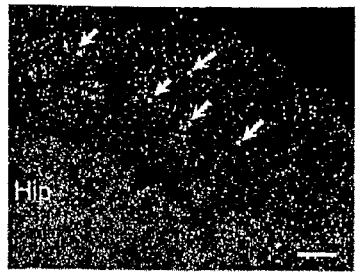
Figure 6O:
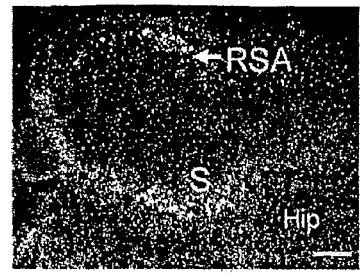

The NPSR mRNA is widely expressed in many brain regions. The strongest expression signals were found in several discrete nuclei or regions such as anterior olfactory nucleus (FIG. 6B), dorsal and ventral endopiriform nucleus (FIG. 6B, C, E, H, I, K), amygdala (FIG. 6H, I), precommissural nucleus, paraventricular thalamic nucleus and subiculum (FIG. 6K, L). High levels of expression were also observed in cortical regions. Motor cortex 2 and retrosplenial agranular cortex are distinct areas in cortex that show strong expression of NPSR mRNA (FIG. 6E, H, K, M, O). Medium levels of expression are also found in dispersed neurons in other cortical regions such as somatosensory cortex (FIG. 6N). High level of expression was found in multiple nuclei of the hypothalamus (FIG. 6H, K). Moderate NPSR expression was also found in midbrain. Pons and medulla are brain regions that express NPSR mRNA only weakly (data not shown).

These data suggest that NPS could be involved in a variety of brain functions. Interestingly, NPSR mRNA is not detected in LC area. However, significant NPSR expression is also found in thalamic midline nuclei such as central medial thalamic nucleus, interanteriomedial thalamic nucleus, reuniens and rhomboid thalamic nucleus (FIG. 6E), which relay extensive inputs from brain stem reticular formation to diffuse cortical fields and are involved in regulation of arousal and wakefulness (Van der Werf et al., 2002).

NPS Increases Locomotor Activity and Promotes Wakefulness

Figure 7A:
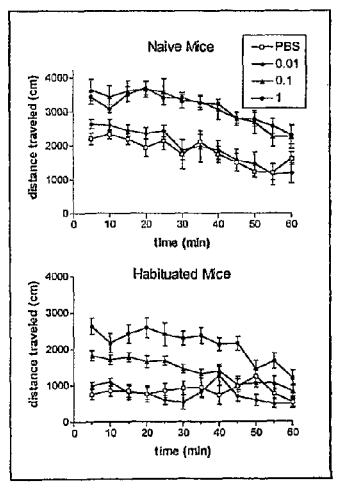
FIGS. 7A and 7B show the effects of central administration of NPS produces behavioral arousal and wakefulness. (A) Hyperlocomotion effects of NPS in naïve and habituated mice. Naive mice were new to the test chamber while habituated animals were acclimatized for one hour prior to the injection. In naive mice, 0.1 and 1 nmole NPS induce significant hyperlocomotion [$F_{3,324}$=92.83, $p<0.0001$, two-way ANOVA for repeated measures]. The same doses of NPS also produced significant effects in habituated animals [$F_{3,336}$=135.59, $p<0.0001$]. (B) Arousal promoting effects of NPS in rats. NPS increases the amount of wakefulness and decreases SWS1, SWS2 and REM sleep in rats (n=8 for each dose). ** $p<0.01$, 0.1 nmole and 1.0 nmole compared with saline; * $p<0.01$, 1.0 nmole compared with saline (ANOVA followed by Scheffe's post hoc test).

In view of the NPSR sites of expression and the prominent expression of the NPS precursor in LC area, we hypothesized that NPS may be involved in arousal and anxiety. To start this investigation, we tested the effects of NPS on locomotor activity in both naive and habituated mice (FIG. 7A). 0.1 nmole or 1 nmole NPS administered intracerebroventricularly (i.c.v.) caused a significant increase in locomotor activity in both naïve and habituated mice (p<0.01) during the 60 min observation period, while 10 pmoles NPS did not. The total distance traveled, percentage of time moving, number of rearing events and center entries were also significantly increased in mice injected with 0.1 and 1 nmole NPS (data not shown). The elevation of locomotor activity in habituated animals indicates that NPS may produce behavioral arousal independent of novelty or stress.

Figure 7B:
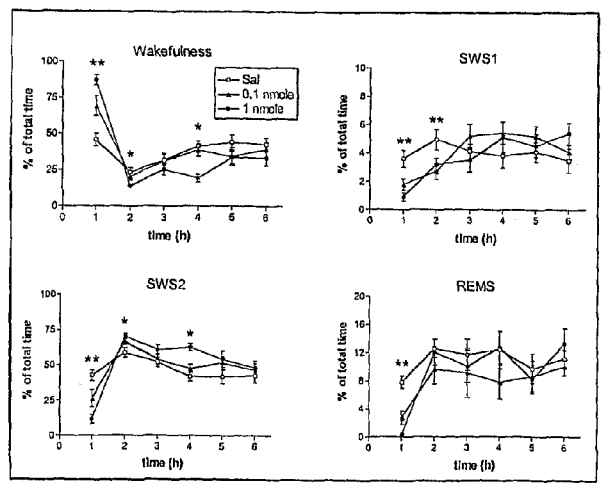

The effects of NPS on locomotor activity suggest a possible role of NPS in modulating sleep-wake patterns. Rats were implanted with a standard set of electrodes and electroencephalograms (EEG) and electromyograms (EMG) were recorded after i.c.v. administration of NPS. Polygraphic recordings of vigilance states indicate that rats treated with 0.1 nmole and 1.0 nmole of NPS spent up to 69% and 87%, respectively, of the first hour of recording in wakefulness, compared to 45% for saline treatment ($F_{2,21}$=16.80; p<0.01) (FIG. 7B). In contrast, the amount of slow wave sleep stage 1 (SWS1) ($F_{2,21}$=9.69; p<0.01), stage 2 (SWS2) ($F_{2,21}$=11.859; p<0.01) and REM sleep ($F_{2,13}$=12.29; p<0.01) in NPS treated rats was significantly reduced compared with saline treated animals. The increase in wakefulness was due to a significant increase in the mean duration of the episodes ($F_{2,21}$=7.22; p<0.01), compared to saline group. Interestingly, the increase in wakefulness during the first hour post NPS injection was followed by a rebound in the amount of non-REM sleep at the second hour (20% increase vs. saline ($F_{2,21}$=5.44; p<0.01)) and fourth hour (48% increase compared to saline treated animals ($F_{2, 21}$=12.22; p<0.01)). Together, these data show that NPS can promote arousal and might be involved in the induction of wakefulness or suppression of sleep.

NPS Attenuates Anxiety-like Behavior

Figure 8A:
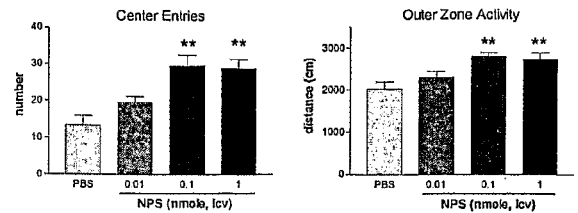
FIGS. 8A-8D are graphs showing the anxiolytic-like effects of NPS in mice. NPS produces dose-dependent anxiolytic-like effects in C57Bl/6 mice exposed to the open field (A), light-dark box (B), elevated plus-maze (C) and marble-burying paradigm (D). Doses and groups: all doses are in nmole per animal; open field (n8 for each dose); light-dark box (PBS, n=10; 0.01 nmole, n=5; 0.03 nmole, n=5; 0.1 nmole, n=5, 0.3 nmole, n=11; 1 nmole, n=5; 3 nmole, n=8); elevated plus-maze (n=5 for all doses); marble burying (PBS and 0.01 nmole, n=10; 0.1 and 1 nmole, n=9). ** $p<0.01$, * $p<0.05$ compared to PBS control, ANOVA followed by Dunneft's test for multiple comparisons. All data are presented as means±SEM.
Figure 8B:
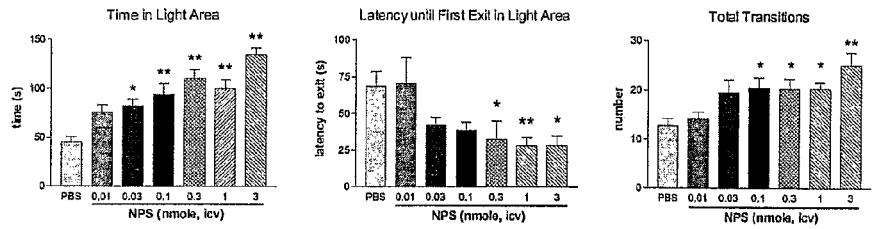

The expression of NPSR in several brain regions that are known to be involved in anxiety such as amygdala, thalamus and hypothalamic regions indicates that the NPS system could also play a role in behavioral response to stress (Charney and Deutch, 1996; Redmond and Huang, 1979; Sah et al., 2003). Naïve mice were tested in the open field, a paradigm of free exploratory behavior in a novel environment. It was found that NPS significantly increased the number of entries in the central zone during the first 10 minutes, which could indicate an anxiolytic-like effect ($p<0.05$; FIG. 8A). However, the same doses of NPS also increased ambulations in the outer zones of the open field, consistent with the arousal-promoting effect of the peptide. In order to further study NPS effects on stress as it relates to anxiety, two additional tests were performed that are based on the natural aversion of rodents to open or unprotected spaces: the light-dark box and the elevated plus maze (FIG. 8B, C). Mice injected with NPS exhibited a dose-dependent reduction in anxiety-like behavior in both paradigms.

Figure 8C:
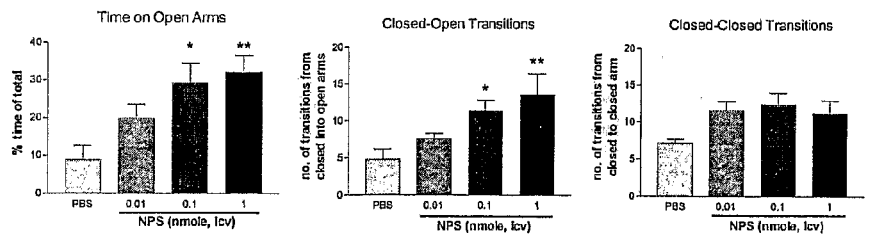

In the light-dark box, mice injected with NPS at a dose range of 0.03- 3 nmole, but not at 0.01 nmole, spent a prolonged time in the light area ($p<0.05$-0.01, FIG. 8B) and showed a higher percentage of entries in the light area (data not shown). The latency until the first exit from the protected dark compartment was significantly reduced by NPS at doses between 0.3-3 nmole. General activity was also enhanced as the number of transitions between the two compartments significantly increased at doses between 0.1-3 nmole. In the elevated plus maze, mice injected with 0.1 and 1 nmole NPS, but not at 0.01 nmole, spent significantly more time on the open arms ($p<0.05$, FIG. 8C) and showed a higher number of transitions from closed to the open arms ($p < 0.05$-0.01). The average number of transitions between the two closed arms of the elevated plus maze (closed-closed transitions) was increased at all doses, but did not reach statistical significance. Closed-closed transitions are a measure of general activity in this behavioral paradigm, so our data indicate that in the elevated plus maze NPS may not produce significant hyperlocomotion. Together, the increased number of entries and prolonged time spent in the unprotected zones of both paradigms (open arm/light area) suggest that central administration of NPS produces an anxiolytic-like effect. However, consistent with the hyperlomocotor effect of NPS as described above, these NPS doses (>0.1 nmole) also significantly increased the total activity in both tests.

Figure 8D:
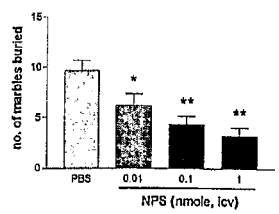

Many anxiolytic drugs increase exploratory activity in the open field, light-dark box or elevated plus maze paradigms. However, compounds stimulating locomotion could produce false-positive effects in these tests because the enhanced exploration could be secondary to the increase in general activity. In order to validate the observed anxiolytic-like effects of NPS, we tested increasing doses of NPS in the marble-burying paradigm. Mice tend to bury objects such as glass marbles present in their environment. Anxiolytic drugs such as benzodiazepines reduce the number of marbles buried over a fixed period of time. It has been suggested that the inhibition of marble-burying behavior is correlated with anxiolytic-like activity (Njung'e and Handley, 1991). As shown in FIG. 8D, mice injected with saline covered about 50% of the marbles during the 30 min observation period (total of 18 marbles per cage). NPS dose-dependently reduced the number of marbles buried. NPS-injected mice were actively exploring the marbles and eventually engaged in burying them, however at significantly lower numbers as compared to mice injected with saline ($p<0.05$-0.01). In summary, the combined results of all four paradigms measuring anxiety-like behavior suggest that NPS might produce anxiolytic-like effects in the presence of increased arousal.

The effects of NPS on inducing wakefulness are rapid (during the first hour after injection) and potent since low doses of NPS are sufficient to reduce all sleep stages such as REM, SWS1, and SWS2, suggesting a profound change in sleep architecture. Recently, the neuropeptide hypocretin 1/orexin A (Hcrt/Ox) has also been demonstrated to induce arousal and genetic analysis has provided compelling evidence that absence of Hcrt/Ox or its receptor(s) produces narcolepsy in mice, dogs and humans (Sutcliffe and de Lecea, 2002). Single i.c.v. injection of Hcrt/Ox produces arousal lasting for 2-3 hours (Bourgin et al., 2000; Hagan et al., 1999) whereas comparable NPS administrations show a more short-term effect within the first hour post injection. Both peptides appear to increase wakefulness while suppressing REM sleep and deep sleep (SWS stage 2) (Bourgin et al., 2000), although one study could not detect a significant effect of Hcr/Ox on deep sleep duration (Hagan et al., 1999). Hcrt/Ox appears to exert its effects partially by directly activating noradrenergic LC neurons since orexin 1 receptors are found to be colocalized with TH in LC neurons and electrophysiological recordings from LC neurons show excitatory effects of exogenously applied Hcrt/Ox (Bourgin et al., 2000). However, the arousal-promoting effect of NPS is unlikely mediated by direct activation of noradrenergic systems since our anatomical data show that NPS expressing neurons do not produce NA and no NPSR mRNA was detected in LC neurons. However, we cannot rule out an indirect activation of noradrenergic systems. Electrophysiological recording will be necessary to confirm a possible link between NPS and monoaminergic transmitter systems that have been implicated in the neurochemistry of wakefulness and arousal.

One unexpected outcome of this study is the discovery of a cluster of NPS expressing neurons that do not produce NA or CRF and are localized in close proximity to the LC proper and Barrington's nucleus. The cluster of NPS expressing neurons is likely to be a previously uncharacterized population of cells in the peri-LC area. Noteworthy, it has been reported before that a large number of uncharacterized neurons are found in the peri-LC area (Aston-Jones et al., 1991b; Rizvi et al., 1994) and our present data suggest that the NPS neuronal cluster could be a subset of these neurons.

It is well documented that the noradrenergic LC is involved in the regulation of an aroused state of wakefulness (Berridge and Waterhouse, 2003). On the other hand, several studies found no major disruption of EEG activity after selective cytotoxic lesions of TH-positive LC neurons or genetic ablation of the noradrenaline-synthesizing enzyme dopamine beta-hydroxylase (Cirelli et al., 1996; Hunsley and Palmiter, 2003), underscoring the fact that arousal is modulated by multiple neuronal systems. Our present data provide evidence that NPS could be a novel arousal-modulating transmitter system. Interestingly, the close vicinity of NPS producing neurons and the noradrenergic neuronal cluster in LC indicate that this brainstem area might contain two independent transmitter systems that regulate vigilance states.

Central administration of NPS produces anxiolytic-like effects but also increases locomotor activity at similar doses. In the open filed, elevated plus maze and light dark box paradigms, increases in exploration are generally interpreted as an anxiolytic effect but the interpretation might be confounded by hyperlocomotion. Factor analysis, however, has shown that the behavioral parameters monitored in these tests can be divided into two components: an activity component (total distance traveled, number of transitions) and an anxiety component (number of entries in unprotected zone, time spent in unprotected zone) (Rodgers and Johnson, 1995) and that these two components show poor correlation. For example, both the psychostimulants amphetamine and cocaine produce hyperlocomotion yet increase anxiety-like behavior, i.e. they are anxiogenic (Hascoet and Bourin, 1998; Paine et al., 2002). On the other hand, the wake-promoting neuropeptide Hcrt/Ox enhances arousal and hyperlocomotion and suppresses REM sleep, but has no effect on anxiety-like behavior in rodents (Hagan et al., 1999). Moreover, typical anxiolytic drugs, such as benzodiazepines, have either no effect or reduce locomotor activity, depending on the doses used (Chaouloff et al., 1997). Therefore, although we acknowledge the possible confounding effects of hyperlocomotion, we suggest that the increased exploratory activity observed in mice after NPS administration may indicate an anxiolytic-like profile in these three paradigms. To further investigate the possible anxiolytic-like effects of NPS, we used the marble-burying test as an alternative behavioral paradigm. In this test, the selective suppression of marble burying behavior is suggested to correlate with anxiolytic activity, in contrast to the other three paradigms where increases of natural behaviors are an index of anxiolytic-like effects. Numerous drugs clinically effective in the treatment of anxiety disorders such as benzodiazepines or selective serotonin reuptake inhibitors reduce marble burying behavior in rodents (Borsini et al., 2002). Our data demonstrate that NPS also inhibits this natural behavior at doses which increase locomotion. Altogether, central administration of NPS reduces behavioral signs of anxiety in four different anxiety tests. These findings indicate that NPS could be involved in modulating anxiety responses.

Thus, central administration of NPS produces a unique behavioral profile by increasing locomotor activity and wakefulness in rodents. NPS could also exert anxiolytic-like effects. In addition, we identify a previously undescribed group of neurons adjacent to the noradrenergic LC that express NPS. The discovery of this novel transmitter system that modulates sleep-wake cycles and anxiety might help to further our understanding of sleep disorders, such as insomnia, and pathological states of anxiety. It should be noted that excessive anxiety and disruption of sleep patterns are often observed in patients suffering from depression and, thus, the methods of the present invention may also be useable in the treatment of depression and/or depression related anxiety or sleep disturbances.

Molecular Cloning of Human NPSR and Rat NPS Precursor

Human NPSR was cloned into pcDNA3.1(+) from human brain cDNA (Clontech, Carlsbad, Calif.) using nested PCR. Primers were 5'-aggagcaaggacagtgaggctcaa-3' (SEQ ID NO: 11) and 5'-tgcccaagcaggtgacaaggacct-3' (SEQ ID NO: 12) for first round amplification and 5'-atactcgagccatgccagccaacttca-cagagggca-3' (SEQ ID NO: 13) and 5'-gcttctagagctcagcctag-cactggcactgcccta-3' (SEQ ID NO: 14) for second round. Rat NPS precursor cDNA was cloned into pBluescript from a rat total brain cDNA library (Clontech). First round amplification primers were 5'-cagattttgggaagtcca-3' (SEQ ID NO: 15) and 5'-agattaattccccgagtc-3'; (SEQ ID NO: 16) second round primers were 5'-gtttctagaaatgattagctcagtaaaactcaa-3' (SEQ ID NO: 17) and 5'-gcagaattcgtcatgattttgctctttgaaagg-3' (SEQ ID NO: 18). The cloned DNAs were sequenced on both strands.

Cell Transfection and Intracellular $Ca^{2+}$ Measurement

HEK 293T cells and CHO dhfr(−) cells were transfected with the human NPSR cDNA cloned into pcDNA 3.1(+) using LipofectAmine. Stable clones were selected with 800 mg/l G418 and tested for mobilization of intracellular $Ca^{2+}$ with 100 nM NPS (generous gift of Phoenix Pharmaceuticals, Belmont, Calif.). Changes in intracellular $Ca^{2+}$ were measured in a fluorometric imaging plate reader system (FLIPR, Molecular Devices) as described before(Saito et al., 1999). Dose response curves for agonist activation were calculated from peak fluorescence values of triplicate incubations and $EC_{50}$ values were calculated with Prism software (GraphPad, San Diego, Calif.).

Radioligand-binding Assay $Y^{10}$-NPS was labeled with $^{125}I$ using the chloramine T method and purified by reversed-phase HPLC in a collaboration with NEN Perkin Elmer (Boston, Mass.). CHO cells stably expressing human NPSR were seeded into 24-well plates and cultured for 48 hours. For saturation binding experiment, [$^{125}I$] $Y^{10}$-NPS at concentrations from 4 pM to 1.7 nM were used. For displacement binding, increasing concentrations of unlabelled human NPS (1 pM to 3 µM) were used to compete with 0.15 nM [$^{125}I$] $Y^{10}$-NPS. Nonspecific binding was determined in the presence of 1 µM unlabeled human NPS. The binding assay was carried out as described (Sakurai et al., 1998). In brief, cells were washed with PBS first and then incubated with radioligand with or without unlabeled NPS peptide in DMEM medium containing 0.1% bovine serum albumin at 20° C. for 1.5 h. Cells were washed 5 times with cold PBS and lysed with 1 N NaOH. Bound radioactivity was counted in a MicroBeta liquid scintillation counter (EG&G Wallac, Gaithersburg, Md.) and corrected for counting efficiency. Data from triplicate incubations were analyzed using PRISM.

Quantitative Real-time PCR

Tissue was collected from male and female adult Sprague Dawley rats and RNA was extracted with Trizol. PolyA+ RNA was prepared using OligoTex (Qiagen) and converted to cDNA using oligo dT and random primers with Superscript reverse transcriptase (Invitrogen). Primers for NPSR (5'-tg-cagggagcaaagatcaca-3' (SEQ ID NO: 19) and 5'-aatctgcatct-catgcctctca-3'(SEQ ID NO: 20)), NPS precursor (5'-tgtcgct-gtccacaatgcat-3' (SEQ ID NO: 21) and 5'-aatcagattttccagacaccttagaag-3' (SEQ ID NO: 22)) and β-actin (5'-cacggcatcgtcaccaact-3' (SEQ ID NO: 23) and 5'-agccacacgcagctcattg-3' (SEQ ID NO: 24)) were predicted using ABI Prism Primer Select software and tested for linearity of amplification using cloned cDNAs as template. Quantitative real-time PCR was performed in an ABI Prism 7000 using SYBR Green PCR Master Mix (Applied Biosystems).

In Situ Hybridization

A 326 bp fragment of the rat NPSR (corresponding to nt 408-734) was amplified by PCR and subcloned into pBluescript SK. A fragment of the rat NPS precursor (corresponding to nt 92-276) was cloned into the same vector. Sense and antisense riboprobes were labeled with $^{35}S$-UTP. Rat tyrosine hydroxylase (TH) cDNA was a gift from Dr. Francis Leslie (UCI) and cloned in pBluescript. Rat corticotropin-releasing factor (CRF) cDNA was a gift from Dr. Christine Gall (UCI) and cloned in the same vector. For double in situ hybridization, antisense TH riboprobes or CRF riboprobes were labeled with digoxigenin using DIG RNA labeling kit (Roche Applied Science). In situ and double in situ hybridization to 20 µm coronal sections of adult Sprague Dawley rat brains was carried out as described before (Clark et al., 2001).

Behavioral Studies.

Male C57Bl/6 mice (National Cancer Institute, Bethesda, MD), age 10-14 weeks, were group-housed (4 animals per cage) under controlled conditions (temperature 21±2° C.; relative humidity 50-60%; 12-hour light-dark cycle, lights on 6:00 AM) with free access to food and water. Prior to drug injections, mice were briefly anesthetized with halothane. NPS was dissolved in phosphate-buffered saline (PBS, pH 7.4) and injected i.c.v. (total volume: 2 µl) as described before (Laursen and Belknap, 1986). Mice were allowed to recover for 5 min and then placed in the observation apparatus.

For sleep studies, adult male Sprague-Dawley rats (250-300 g) were implanted under halothane anesthesia (1-2%) with a stainless steel cannula for i.c.v. administration and a standard set of stainless steel screw electrodes for chronic sleep recordings as reported previously (Bourgin et al., 2000).

Rats were injected with NPS or vehicle (5 μl) at the beginning of the light cycle and cortical activity was recorded over 6 hours. All animal experiments had been approved by the local IACUC committee and were done in accordance with federal regulations and guidelines on animal experimentation.

Locomotion was monitored in rectangular plexiglass boxes (60×40×50 cm). Horizontal activity was measured over 60 min by 18×12 infrared sensors placed 2 cm above the floor. A second row of sensors at 8 cm above the floor was used to record rearing events. The imaginary central zone was defined as a 30×20 cm rectangle in the middle of each observation area. Data were collected using MatLab (Mathworks, Natick, Mass.). Experimental procedures for open field, elevated plus-maze and light-dark box were described previously (Köster et al., 1999). Marble burying was measured in mice placed individually in polypropylene cages (30×18×12 cm) containing 18 glass marbles (1.5 cm diameter) evenly spaced on 5 cm deep rodent bedding (bed-o'cob, The Andersons Inc., Maumee, Ohio) (Njung'e and Handley, 1991). No food or water was present during the observation period. Cages were covered with a metal grid and the number of marbles covered at least two-thirds was counted after 30 min.

Applicants have determined that a number of single-nucleotide polymorphisms in the NPSR gene are associated with increased risk of asthma and possibly other forms of atopic diseases but the physiological consequences of the mutations remain unclear. As explained in the following paragraphs, one of the polymorphisms produces an Asn-Ile$^{107}$ exchange in the second extracellular loop of the receptor protein and a C-terminal splice variant of the NPSR was found over-expressed in human asthmatic airway tissue. Described herebelow are studies wherein the two receptor variants of the NPSR were compared with the wildtype protein. The Asn-Ile$^{107}$ polymorphism is determined to result in a gain-of-function characterized by an increase in agonist potency without changing binding affinity. In contrast, the C-terminal splice variant of the NPSR shows a pharmacological profile similar to the wildtype receptor. The altered pharmacology of the Ile$^{107}$ isoform of the NPSR implies a physiological mechanism of enhanced NPS signaling that could contribute to the pathophysiological changes observed in asthmatic airway tissue.

Asthma is characterized by increased constriction of smooth muscles in bronchial airways, airway inflammation accompanied by activation of macrophages and mast cells followed by mucus hypersecretion and finally airway remodeling. Therapeutically, reduction of smooth muscle tone by adrenergic agonists and suppression of inflammatory processes by glucocorticoids and cysteinyl-leukotriene receptor (CysLT) antagonists remain the preferred treatment options, although both strategies are only symptomatic. A number of mechanisms have been discussed regarding the pathophysiology of asthma. Large epidemiological studies have pointed at both genetic and environmental factors to increase the risk of developing asthma and recent efforts in positional cloning have identified a number of candidate genes that might represent susceptibility factors. However, in most cases the physiological function of these candidate genes and their mechanism of action remain elusive.

Very recently, a G protein-coupled receptor was identified in Finnish and Canadian asthma patients that was linked to an increased susceptibility for asthma and potentially other forms of allergy that are characterized by high IgE serum levels. The study described a number of risk haplotypes and originally termed the receptor "GPRA isoform A" (for G protein-coupled receptor associated with asthma, GenBank accession no. NP_997055; the protein has also been termed GPR 154). This receptor protein is identical to the NPSR that we have studied extensively for its pharmacology, distribution and function in brain. A single-nucleotide polymorphism associated with the increased risk haplotype changes the primary structure of the receptor protein to code for an Asn-Ile exchange at position 107 of the mature protein (SNP591694 A>T; refSNP ID: rs324981). The study also found that a C-terminal splice variant of the receptor, originally termed "GPRA isoform B" (GenBank accession no. NP_997056), was over-expressed in human asthmatic airway tissue and that the orthologous murine receptor mRNA was upregulated in a mouse model of chronic airway inflammation. Most importantly, bronchial smooth muscle cells were shown to express the receptor, indicating a potential role in bronchial constriction. De novo expression of the C-terminal splice variant was detected in asthmatic bronchial biopsies while expression levels of the wildtype receptor protein (synonymous: GPRA isoform A) were significantly lower in healthy airway smooth muscle. These data strongly suggest a possible involvement of the mutant receptor in the pathophysiology of asthma, but the report by Laitinen et al. did not describe a functional role for the receptor or its isoforms due to the lack of a pharmacologically useable agonist.

Naturally occurring NPS is a peptide whose conserved structure carries an aminoterminal serine residue in all species thus far examined. The primary structure of the wildtype NPSR (NPSR WT) is identical to isoform A of GPRA. The receptor variant containing isoleucine at position 107 is referred to in this patent application as "NPSR Ile$^{107}$" (NPSR Ile$^{107}$) and the splice variant containing an alternative C-terminal exon is termed "NPSR C-alt."

In initial studies Applicants found that NPSR is widely expressed in the rat brain while the NPS precursor mRNA is found in only a few brain structures. Highest levels of NPS precursor expression were detected in a novel nucleus located in between the noradrenergic locus coeruleus and Barrington's nucleus in the pontine area of the rat brain stem. Other brain regions of high NPS precursor expression include the lateral parabrachial nucleus, sensory principle 5 nucleus and a few scattered neurons in the amygdala and dorsomedial hypothalamic nucleus. In addition, we found high expression of NPS and NPSR mRNA in endocrine tissues including thyroid, mammary and salivary glands but did not observe significant levels in rat lung tissue.

Central administration of NPS promotes behavioral arousal and suppresses all stages of sleep in rodents. Furthermore, NPS was found to produce anxiolytic-like effects in a battery of four different tests that measure behavioral responses of rodents to stress. NPS was shown to induce transient increases of intracellular $Ca^{2+}$, indicating that it might have excitatory effects at the cellular level.

Even though a number of polymorphisms were described for NPSR and although each of them could have functional significance, an immediate structural change of the receptor protein is produced by the point mutation at amino acid position 107 (Asn-Ile$^{107}$) and the use of an alternative 3' exon. Therefore, the present study focused on investigating if the point mutation or alternative splicing of NPSR could affect the pharmacological profile of the receptor and if these changes might have functional consequences that could indicate a possible physiological role of NPSR variants in bronchial tissue. In this study we demonstrate that a gain-of-function mutation in NPSR Ile$^{107}$ could explain some of the pathological mechanisms of asthma.

Cloning and Functional Expression of NPSR Isoforms

Human NPSR WT cDNA was cloned using known techniques, as described in Xu, Y.-L., Reinscheid, R. K., Huitron-Resendiz, S., Clark, S. D., Wang, Z., Lin, S. H., Brucher, F. A., Zeng, J., Ly, N. K., Henriksen, S. J., de Lecea, L., and Civelli, O. (2004) *Neuron* Volume 43, Pages 487-497. The Ile$^{107}$ isoform of NPSR was generated by PCR using synthetic oligonucleotides and the Quik Change Site-Directed Mutagenesis kit from Stratagene. The C-terminal splice variant of NPSR (NPSR C-alt) was generated by recombinant PCR. First, the alternatively spliced exon was cloned by PCR from human genomic DNA using primers NPSRB5 (5'-ATCTCTTTCCCCTGCAGGGTCATCCGTCTCC) (SEQ ID NO: 25) and NPSRB3-XbaI (5'-TT TCTAGAGAGCTGTCACCTTGGAA, XbaI site underlined) (SEQ ID NO: 26). Recombinant PCR was carried out with the cloned exon and human NPSR WT as templates using primers NPSRA5-XhoI (5'- ATA CTCGAGCCATGCCAGCCAACTTCACAGAGGGCA, XhoI site underlined) (SEQ ID NO: 27) and NPSRB3-XbaI. The products were gel-purified and cloned into pcDNA3.1 hygro (Invitrogen). Transfection of CHO and HEK 293 cells was carried out using lipofectamine (Life Technologies) as described in Xu, Y.-L., Reinscheid, R. K., Huitron-Resendiz, S., Clark, S. D., Wang, Z., Lin, S. H., Brucher, F. A., Zeng, J., Ly, N. K., Henriksen, S. J., de Lecea, L., and Civelli, O. (2004) *Neuron* Volume 43, Pages 487-497. Selection of stable clones was achieved by culturing transfected cells in medium containing 400 mg/l hygromycin (Omega Scientific, Tarzana, Calif.). For transient expression, transfected cells were cultured for 72 hours without antibiotic selection.

Detection of Endogenous NPSR Expression in Cell Lines

Total RNA from a number of human cell lines (HEK293, U373, 1321N, Caco-2, LoVo, DLD-1, Colo205, HT-29, SW480, SW1116, HCT116) was extracted and converted into single-strand cDNA using reverse transcriptase (New England Biolabs) and oligo dT primers. Quantitative real-time PCR was carried out as described using primers specific for human NPSR.

Measurement of Intracellular $Ca^{2+}$ Mobilization

Changes of agonist-induced intracellular $Ca^{2+}$ were measured using the FLIPR technology as described before (5, 6). NPS and truncated NPS peptides were a gift from Phoenix Pharmaceuticals (Belmont, Calif.). Dose-response curves were calculated using GraphPad Prism (Graph Pad, San Diego). Mean $EC_{50}$ values of populations of stable clones expressing either wildtype or mutant NPSR were compared using unpaired t-test and $p<0.05$ was considered significant.

Measurement of cAMP Accumulation

Accumulation of cAMP was measured in accordance with known technique. Stably transfected cells were seeded into 24-well plates and cultured for 24 hours. Culture medium was aspirated and exchanged for 200 µl Opti-MEM (Life Technologies) containing 100 µM 3-isobutyl-1-methylxanthine and agonists at various concentrations. After incubation for 15 min at 37° C. cells were lysed by adding ethanol to a final concentration of 66%. Aliquots of the lysate were lyophilized and cAMP content was measured in a radioimmunoassay (either Flashplate, NEN Perkin Elmer, or SPA Biotrak, Amersham). Dose response curves were calculated using Graph-Pad Prism.

CRE-Luciferase Reporter Gene Assays

HEK 293 cells were stably transfected with a reporter gene containing 6 copies of a cAMP response element (CRE; sequence CCAAT) in front of a luciferase reporter gene (Promega) cloned into pcDNA3.1 neo. One stable clone showing robust induction of reporter gene expression after forskolin challenge was chosen for further experiments. The different NPSR isoform cDNAs (cloned into pcDNA3.1 hygro) were transfected into these cells using lipofectamine and stable clones were selected. The same cells and procedures were also used for transient transfection. For induction of reporter gene expression cells were plated in 96-well plates and incubated with agonist for 5 hours in serum-free medium, followed by aspiration of the medium and cell lysis with 25 mM Tris-phosphate, pH 7.8, 2 mM dithiothreitol, 2 mM 1,2-diaminocyclohexane-N,N,N',N',-tetraacetic acid, 10% glycerol, 1% Triton X-100. After one freeze-thaw cycle aliquots of supernatant were transferred to white clear-bottom 96-well plates (Greiner) and luciferase content was quantified by bioluminescence (Luc-Screen, Applied Biosystems). Plates were counted in a scintillation counter using bioluminescence settings (MicroBeta, Wallac-Perkin Elmer).

Cell Proliferation Assays

Cells were seeded in 24-well plates and grown overnight to 60-70% confluency. Following 24 h serum-starvation, 2 µCi of methyl-[$^3$H] thymidine was added together with increasing concentrations of NPS. 500 nM $PGE_2$ served as a positive control. After 3 h incubation cells were washed 3 times with PBS and then lysed with 0.5 N NaOH. The lysate was neutralized with 0.5 N HCl and aliquots were counted in a liquid scintillation counter for incorporated radioactivity.

MAP Kinase Phosphorylation

Agonist-induced phosphorylation of p42/p44 mitogen-activated protein kinase (MAPK) was determined as described in Saito, Y., Wang, Z., Hagino-Yamagishi, K., Civelli, O., Kawashima, S., and Maruyama, K. (2001) *Biochem. Biophys. Res. Commun.* Volume 289, Pages 44-50. Briefly, cells were cultured in 24-well plates in serum-free cell culture medium for 24 h. After stimulation for 5 min at 37° C. with increasing concentrations of NPS, cells were washed with phosphate-buffered saline and lysed with 10 mM Tris-HCl, pH 7.5, 150 mM NaCl, 5 mM EDTA, 0.1% SDS, 1.5% Nonidet P-40, 0.5% sodium deoxycholate, 1 mM sodium orthovanadate, 1 mM sodium fluoride, 0.5 mM phenylmethylsulfonyl fluoride, 1 µg/ml aprotinin, 0.5 µg/ml leupeptin, 0.7 µg/ml pepstatin, 100 g/ml bacitracin. Lysates were centrifuged and aliquots of supernatant electrophoresed on 4-10% SDS-polyacrylamide gels. Phosphorylated p42/p44 MAPK was assayed by Western Blot. After transfer to Hybond C membranes (Amersham), blots were incubated with anti-phospho p42/p44 MAPK antibody (Cell Signaling Technologies; dilution 1:1500) in Tris-buffered saline, 1% nonfat dried milk, 0.2% Tween 20 at 4° C. overnight. Horseradish peroxidase-conjugated goat anti-rabbit IgG (Jackson Immuno Research Lab; dilution 1:2000) was used as a secondary antibody. Immunoblots were developed using an Enhanced Chemiluminescence detection kit (Amersham) and films were scanned by densitometry (UN-SCAN-IT; Silk Scientific Inc., Orem, Utah) for quantitative analysis.

Radioligand Binding

Saturation binding experiments in intact cells were carried out as described in Xu, Y.-L., Reinscheid, R. K., Huitron-Resendiz, S., Clark, S. D., Wang, Z., Lin, S. H., Brucher, F. A., Zeng, J., Ly, N. K., Henriksen, S. J., de Lecea, L., and Civelli, O. (2004) *Neuron*, Volume 43, Pages 487-497. $K_d$ and $B_{max}$ of [$^{125}$I] $Y^{10}$-NPS binding were calculated using GraphPad Prism. [$^{125}$I] $Y^{10}$-NPS was a gift from NEN Perkin-Elmer. Non-specific binding was determined in the presence of 1 µM NPS.

NPS produces an increase in intracellular $Ca^{2+}$ in cells stably expressing NPSR WT with an $EC_{50}$ around 5-10 nM. Cells transiently transfected with either wildtype, NPSR Ile or NPSR C-alt cDNAs did not show agonist-induced changes in Ca$^{2+}$ (data not shown). Also, we could not detect significant receptor binding in transiently transfected cells with any of the constructs, indicating that the proteins might be either difficult to express or expressed at low levels. Therefore, we established stable cells lines expressing either NPSR WT or NPSR Ile in HEK 293 cells.

Figure 10A:
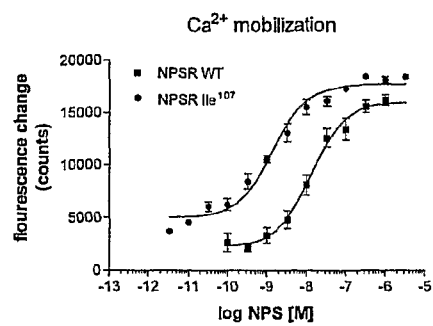
FIGS. 10A and 10B are graphs showing pharmacological activity of NPS at NPSR WT and NPSR Ile$^{107}$. A, dose-response curves of NPS to elicit mobilization of intracellular $Ca^{2+}$ in HEK 293 cells stably expressing either NPSR WT or NPSR Ile$^{107}$. NPS displays greater agonist potency at NPSR Ile$^{107}$. Incubations were performed in triplicate and repeated three times. B, Scatter-plot of logarithmic $EC_{50}$ values of individual HEK 293 clones expressing either NPSR WT or NPSR Ile$^{107}$. Dose-response curves for each single clone were established measuring either mobilization of intracellular $Ca^{2+}$ (left) or induction of luciferase reporter gene transcription (right). Horizontal bars indicate mean $EC_{50}$ values.
Figure 10B:
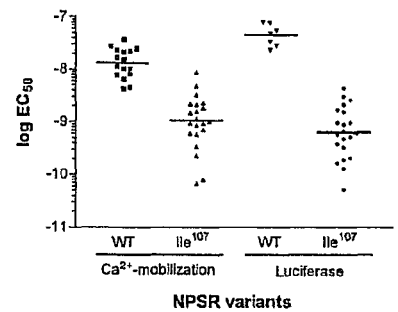

Two cells lines expressing similar levels (measured by radioligand binding; see below) of either NPSR WT or NPSR Ile were chosen for detailed analyses of pharmacological parameters. As shown in FIG. 10A, NPS induced a dose-dependent increase in intracellular free Ca$^{2+}$ in both cell lines. Cells expressing NPSR WT displayed an EC$_{50}$ of 12.4±1.24 nM, whereas the clone expressing NPSR Ile responded to agonist stimulation with an EC$_{50}$ of 1.4±1.17 nM. In order to investigate whether this tenfold increase in agonist potency at NPSR Ile was a general property of the receptor protein we compared a large number of stable clones expressing either NPSR WT or NPSR Ile$^{107}$ by establishing dose-response curves for each construct and calculating mean EC$_{50}$ values for the populations. As shown in FIG. 10B, the mean EC$_{50}$ for NPS-induced mobilization of intracellular Ca$^{2+}$ at NPSR WT was found to be 13.02±1.18 nM (n=16 individual stable clones). In contrast, NPSR Ile$^{107}$ displayed a more than ten-fold lower mean EC$_{50}$ of 1.01±0.13 nM (n=21 individual stable clones). These data demonstrate that NPSR Ile$^{107}$ is activated by significantly lower concentrations of agonist (F=3.365, p=0.0101).

Figure 11A:
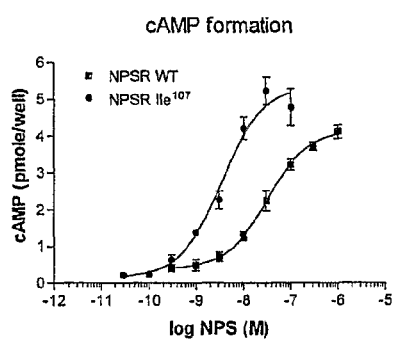
FIGS. 11A and 11B are graphs showing pharmacological profile of NPSR variants stimulating the cAMP pathway. A, dose-response curve of NPS to stimulate cAMP formation in two individual HEK 293 clones expressing either NPSR WT or NPSR Ile$^{107}$. NPS displays greater agonist potency at NPSR Ile$^{107}$. Incubations were performed in triplicate and repeated three times. B, dose-response curves of NPS stimulating CRE-mediated luciferase reporter gene expression. HEK 293 cells were transiently transfected with plasmids containing either NPSR WT, NPSR Ile$^{107}$ or NPSR C-alt cDNA constructs. Bioluminescence was determined from triplicate incubations repeated at least twice.

Using the same approach as described before, Applicants compared the EC$_{50}$ values of a large number of stable clones established in HEK cells that co-express the CRE-Luciferase reporter gene. As shown in FIG. 10B, HEK cells stably expressing both the wildtype NPSR and the reporter gene displayed a mean EC$_{50}$ of 45.08±1.19 nM for NPS-induced reporter gene expression (n=7 individual clones). In contrast, cells co-expressing NPSR Ile$^{107}$ and the reporter gene showed a mean EC$_{50}$ of 0.63±0.43 nM for NPS (n=21 individual stable clones). Again, these data indicate that NPSR Ile$^{107}$ is activated at significantly lower agonist concentrations than the wildtype receptor (F=5.854, p=0.0183). Since expression of the reporter gene is proportional to the amount of activated CREB protein binding to the CRE sequences within the reporter gene promotor, these data also suggest that NPSR is able to signal via G$_s$-type of G proteins to increase cAMP formation. We confirmed this hypothesis by directly quantifying cAMP levels in the two stable clones that were used previously to establish dose-response relationships for mobilization of intracellular Ca$^{2+}$. As shown in FIG. 11A, NPS induced cAMP accumulation in HEK cells stably expressing the wildtype receptor with an EC$_{50}$ of 31.9±1.17 nM. In HEK cells expressing NPSR Ile$^{107}$, NPS stimulated cAMP formation at about ten-fold lower agonist concentrations with an EC$_{50}$ of 3.45±1.26 nM.

Figure 11B:
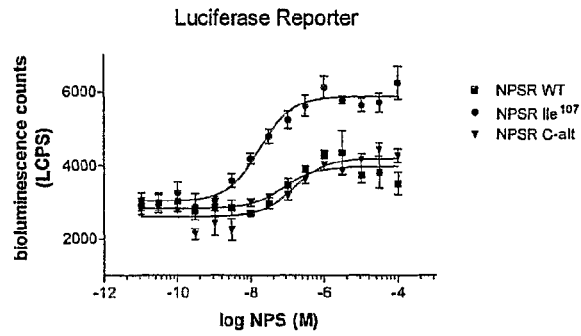

As mentioned above, it was not possible to observe second messenger signaling in transiently transfected cells measuring either mobilization of Ca$^{2+}$ or formation of cAMP. However, due to the high rate of signal amplification of the luciferase reporter gene assay, it was possible to establish agonist dose-response curves with this assay in transiently transfected cells. As shown in FIG. 11B, the wildtype NPSR displayed only a weak induction of luciferase activity with an EC$_{50}$ of 76.6±21.5 nM. In contrast, NPSR Ile produced a robust increase in reporter gene expression with an EC$_{50}$ of 17.3±1.31 nM. The NPSR variant containing the alternatively spliced C-terminus (NPSR C-alt) displayed an EC$_{50}$ of 146.5±15.1 nM, very similar to the wildtype NPSR. The maximum of reporter gene expression in HEK cells transiently transfected with NPSR Ile$^{107}$ was about 2 fold higher than in cells expressing NPSR WT or NPSR C-alt, suggesting an increase in agonist efficacy as well as total receptor number. The magnitude of reporter gene induction was about 20-fold lower in transiently transfected cells as compared to stable clones. Taken together, these data indicate that the Ile mutation produces a gain-of-function in the NPSR protein, whereas the alternatively spliced C-terminus does not appear to affect second messenger coupling of the receptor.

Figure 12A:
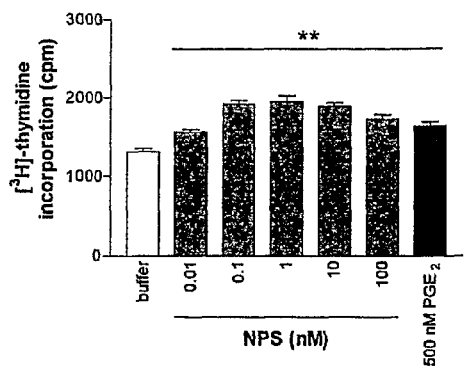
FIGS. 12A and 12B NPS effect on cell proliferation and MAPK phosphorylation. A, NPS-induced stimulation of [$^3$H]-thymidine incorporation in Colo205 human colon cancer cells. NPS produces a dose-dependent stimulation of cell proliferation. 500 nM $PGE_2$ was used as a positive control. All incubations were performed in triplicates and experiments were repeated twice. ** $p<0.01$ vs. buffer control. B, stimulation of MAPK phosphorylation by increasing concentrations of NPS. Values were normalized to levels of phospho-MAPK produced by incubation with 1 μM NPS (=100%). Phospho-MAPK was quantified by densitometric scanning of Western Blots as described under "Materials and Methods". Assays were performed in duplicate and repeated twice.
Figure 12B:
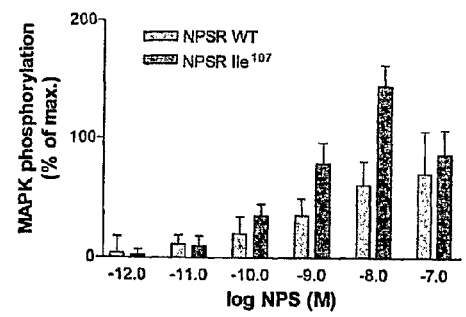

Chronic asthma is accompanied by airway tissue remodeling, involving proliferation of smooth muscle cell layers and basement membrane hyperplasia. In order to investigate whether NPSR can affect cell proliferation at natural levels of receptor expression, we screened a number of cancer cell lines for endogenous NPSR mRNA expression by RT-PCR. The human colon cancer line Colo205 was found to express NPSR transcripts but did not display agonist-induced second messenger responses (data not shown). However, NPS produced a dose-dependent stimulation of thymidine incorporation in Colo205 cells, indicating that the peptide can stimulate cell proliferation and mitogenic signals in these cells (FIG. 12A). Doses of 0.1-10 nM NPS produced maximal thymidine incorporation, exceeding the effect of the well-characterized mitogen prostaglandin E2 on these cells. The human colon cancer cell line DLD-1, which does not express NPSR transcripts, served as a negative control and showed no NPS-dependent thymidine incorporation (data not shown). We next examined potential intracellular mediators of the proliferative response elicited by NPS. The p42/p44 mitogen-activated protein kinase (MAPK) is a well-known integrator of mitogenic signals and many GPCRs have been shown to increase phosphorylation of MAPK upon agonist stimulation. We found that NPS can stimulate MAPK phosphorylation in a dose-dependent manner in HEK cells stably expressing NPSR WT or NPSR Ile$^{107}$ isoforms. As observed before, NPS was more potent to induce MAPK phosphorylation in cells expressing NPSR Ile$^{107}$ (EC$_{50}$: 0.32±0.25 nM) than in cells expressing NPSR WT (EC$_{50}$: 1.23±0.38 nM) (FIG. 12B).

Figure 13A:
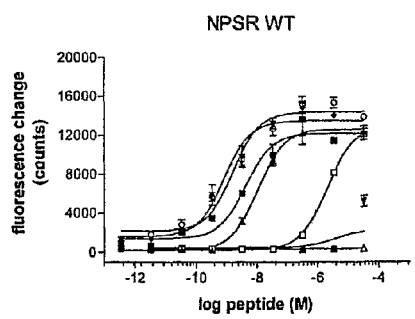
FIGS. 13A and 13B are graphs showing structure-activity relationships of NPS peptides and truncated NPS fragments at human NPSR variants. $Ca^{2+}$ mobilization elicited by human (h), mouse (m) or rat (r) NPS and various NPS fragments was determined in two individual HEK 293 clones expressing either NPSR WT (13At) or NPSR $Ile^{107}$ (13B). Dose-response curves were calculated from triplicate incubations and all assays were repeated at least twice. See Table 1 for comparison of $EC_{50}$ values and peptide sequences.
Figure 13B:
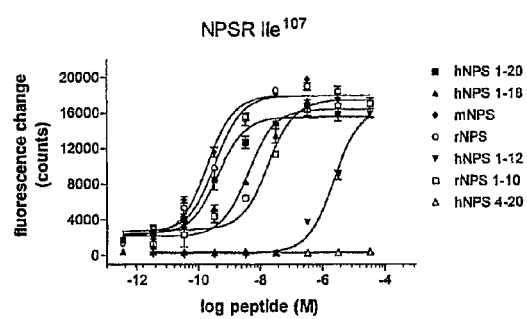

Two individual clones, expressing either NPSR WT or NPSR Ile$^{107}$ with EC$_{50}$ values close to the average EC$_{50}$ in mobilizing intracellular Ca$^{2+}$, were chosen to examine the structure-activity relationships of various NPS fragments. These NPS fragments represent potential processing products that could result from proteolytic cleavage or human NPS 1-20. In addition, we also tested the effect of rat and mouse NPS 1-20 on these cells. As shown in FIGS. 9 and 13, most carboxy-terminally truncated fragments of NPS retained full agonist potency at both wildtype and NPSR Ile$^{107}$. Rat and mouse NPS 1-20 appear to be slightly more potent agonists at both NPSR isoforms as compared to the human peptide. Interestingly, NPS 1-12 almost completely lost agonist activity at the wildtype receptor while still behaving as a full, but weakly potent, agonist at NPSR Ile$^{107}$. Further deletion of the two lysine residues (at position 11 and 12) produced NPS 1-10. NPS 1-10 displayed full agonist activity at both NPSR isoforms, albeit with significantly higher potency at NPSR Ile$^{107}$. Deletion of the three amino-terminal amino acids (NPS 4-20) completely abolished agonist activity. These data indicate that the N-terminus of NPS contains the pharmacophore. The two lysine residues at position 11 and 12 appear to prohibit activation of the receptor when exposed at the C-terminus because further C-terminal deletion to NPS 1-10 restored agonist activity. Because of the peculiar pharmacology of NPS 1-12, this fragment was also tested for possible antagonist activity but failed to block activation of the two receptor isoforms by NPS 1-20 (data not shown). Overall, the various NPS fragments display a 5-10 fold higher potency at NPSR Ile$^{107}$ as compared to NPSR WT.

Some of the previous observations could be explained by an increased affinity or receptor expression of NPSR Ile$^{107}$ versus NPSR WT. In view of this, Applicants determined receptor binding parameters in a number of stable clones for both variants. Surprisingly, both NPSR WT and NPSR Ile$^{107}$ bind the radioligand with very similar affinities ($K_d$ range of NPSR wildtype clones: 0.2-0.45 nM, n=4, average $K_d$: 347.1±44 pM; $K_d$ range of NPSR Ile$^{107}$ clones: 0.17-0.4 nM, n=4, average $K_d$: 402.5±49 pM). However, stable NPSR Ile$^{107}$ clones tended to express more functional receptor protein per cell than NPSR WT clones (average $B_{max}$ of NPSR Ile$^{107}$ clones: 12.5±3.5 fmole/10$^5$ cells; average $B_{max}$ of NPSR WT clones: 3.9±1.5 fmoles/10$^5$ cells; n=4 for each receptor variant). It is currently not known how the Asn$^{107}$Ile exchange can influence protein levels in transfected cells. In general, the levels of NPSR expression are low compared to other GPCRs expressed in the same cellular environment. Dose-response relationship experiments for Ca$^{2+}$ mobilization, cAMP formation and MAPK phosphorylation were performed with two individual clones that displayed very similar receptor levels in order to correct for possible confounds caused by varying numbers of functional receptors (FIGS. 10A, 11A, and 12B). Taken together, our data indicate that the increased potency of NPS at NPSR Ile$^{107}$ is not caused by a change in receptor affinity but might reflect an increased intrinsic efficacy of the receptor protein to couple to G proteins and thus to the various second messenger pathways, as described above. In the present study Applicants have investigated the general pharmacological properties of three natural variants of the human NPSR that has been recently identified as an asthma susceptibility gene. Applicants also sought to determine whether the coding polymorphism or alternative splicing of NPSR would affect the receptor pharmacology in a way that might have functional significance for the pathophysiology of asthma.

Applicants' data provide evidence for an increased agonist efficacy at NPSR Ile$^{107}$. Surprisingly, the Asn$^{107}$Ile point mutation does not affect ligand binding affinity, even though this amino acid is expected to be close to the ligand binding pocket of the receptor protein. The endogenous agonist NPS displays about a ten-fold higher efficacy at NPSR Ile$^{107}$ as compared to the wildtype receptor in mobilizing intracellular Ca$^{2+}$, stimulating cAMP formation or inducing MAPK phosphorylation. The Ile$^{107}$ mutation does not produce increased constitutive activity, as judged from the cAMP accumulation and reporter gene assays. A plausible explanation for our observations could be that the Asn$^{107}$Ile polymorphism is producing a conformational change of the receptor protein that facilitates G protein interaction and thus increases agonist efficacy. Also, we observed a trend to higher levels of receptor protein expression in stable clones expressing NPSR Ile$^{107}$. However, it is not known if NPSR Ile$^{107}$ expression is also facilitated in vivo or our observation is due to the over-expression system used in our studies. Together, our data indicate that the Asn$^{107}$Ile polymorphism produces a gain-of-function that could have significant functional consequences with regard to the pathophysiology of asthma.

The receptor protein appears to be expressed in airway smooth muscle cells that might contribute to bronchial constriction. Applicant's data indicate that activation of NPSR produces an increase in intracellular free Ca$^{2+}$ and that the NPSR Ile$^{107}$ variant, when expressed in airway smooth muscle cells, could thus transmit an enhanced contractile response requiring lower agonist concentrations. Since increased bronchial constriction is one of the physiological hallmarks of asthma, the gain-of-function mutation in NPSR Ile$^{107}$ could therefore be associated with this phenotype. Also, our studies provide evidence for a proliferative effect of NPS using a cellular model of endogenous NPSR expression and demonstrating enhanced phosphorylation of MAPK. Tissue remodeling in asthmatic airways involves proliferation of smooth muscle cells and thickening of basal membranes. It remains to be determined whether these pathological changes are influenced by NPSRs endogenously expressed in airway smooth muscle cells.

The C-terminal splice variant of NPSR (NPSR C-alt, GPRA isoform B) was described to be significantly over-expressed in airway smooth muscle cells from asthmatic patients as compared to healthy controls when studied by immunohistochemical staining. Our data provide no evidence for an altered second messenger response elicited by NPSR C-alt as compared to NPSR WT. It remains to be determined whether the alternative C-terminal tail of the receptor protein can affect other signaling pathways and thus have functional significance in the pathology of asthma. However, it seems reasonable to assume that mere over-expression of NPSR C-alt in airway smooth muscle cells well be sufficient to increase NPS signaling and thus lead to enhanced bronchial constriction or tissue remodeling.

At present, the functional involvement of NPSR in airway smooth muscle contraction still remains to be verified. It should also be noted that a recent study failed to detect genetic association of another polymorphic site in the NPSR/GPRA locus on human chromosome 7 (SNP522363 G>C) in Korean patients. Although this polymorphism is located in an intron and distant from the SNP producing the Asn$^{107}$Ile variant (SNP591694 A>T), it was found strongly associated with the risk haplotypes in the original study. Two more recent studies investigating large outbred European populations seem to confirm that SNP522363 is not associated with increased risk of asthma while lending support for the overall observation that specific NPSR haplotypes confer an increased risk of developing asthma. Therefore, further investigations into the functional role of NPSR in asthmatic and healthy lung will be necessary to determine whether the gain-of-function mutation in NPSR Ile$^{107}$ that we describe in this paper is involved in the pathological events underlying asthma. Ultimately the development of NPS antagonists will be a critical step to clarify the contribution of NPS signaling in bronchial constriction. It should also be noted that rat and mice NPSR genes both code for an Ile residue at the corresponding position and do not possess the alternatively spliced exon giving rise to NPSR C-alt. It may therefore be difficult to study the physiological functions of human NPSR variants in these rodent model organisms.

Applicants' data show that NPSR can couple to intracellular Ca$^{2+}$ as well as cAMP pathways, indicating interaction with both G$_q$ and G$_s$ types of G proteins. The pharmacophore of NPS is contained within the N-terminal part of the peptide and we describe NPS 1-10 as a minimally active structure. All NPS fragments used in our studies could be produced by proteolytic processing involving trypsin-like cleavage at basic amino acid residues. Some of these fragments retain potent agonist activity. Therefore, it will be important to determine the enzymatic steps involved in the inactivation of this neuropeptide in vivo. Apparently the NPSR protein cannot be studied easily in transient transfection systems which made the pharmacological analysis of the receptor variants more tedious. One common problem of using stable clones for second messenger assays is caused by the fact that each clone displays an individual pharmacology and comparison of too few stable clones can lead to inaccurate assumptions about general pharmacological properties. Therefore, a large population of stable clones were analyzed and mean $EC_{50}$ values were determined, followed by statistical analysis. This procedure allowed us to detect significant differences in agonist-induced second messenger coupling between NPSR WT and NPSR $Ile^{107}$.

Naturally occurring mutations that affect receptor function have been identified in numerous GPCRs. Not surprisingly, most of these mutations lead to inactive receptor proteins. The few examples of gain-of-function mutations can be divided into two classes based on their pharmacological phenotype: One group of mutations produces constitutively active receptors that promote second messenger signaling in the absence of endogenous agonist. This type of activating mutations has been found in the glycoprotein-hormone receptor subfamily (LH and TSH receptor), parathyroid and parathyroid-related peptide receptor, as well as in rhodopsin. The other type of mutations increases ligand affinity or agonist efficacy in a way similar to the NPSR $Ile^{107}$ variant. Such mutations have been found in the $Ca^{2+}$-sensing receptor and result in hypocalcemia and hypercalciuria.

Genetic variations in several GPCRs have also been associated with asthma susceptibility or effectiveness of asthma pharmacotherapy. A coding polymorphism in the cysteinyl-leukotriene receptor type 2 (CysLT2) was found to reduce the receptor's affinity to one of its major endogenous ligands, leukotriene $D_4$ ($LTD_4$). Since $LTD_4$ is an important mediator of inflammatory responses in asthma this polymorphism in CysLT2 provides an asthma-protective effect. Similarly, particular haplotypes in the promotor region of the prostanoid DP receptor (PTGDR) were found underrepresented in asthmatic patients. These polymorphisms lead to a reduced transcription of the PTGDR mRNA and thus lower levels of receptor protein. Prostaglandin D2 (the endogenous ligand of PTGDR) is an important mediator of asthma and PTGDR was found to be required for the development of airway sensitization in a mouse model of asthma. This explains why reduced levels of PTGDR expression lead to an overall asthma-protective effect. Coding polymorphisms in the $\beta_2$-adrenoreceptor that influence receptor downregulation in response to adrenergic agonists were found to be associated with the therapeutic benefit of $\beta_2$-agonists to treat symptoms of asthma. One study described that patients homozygous for a particular genotype (Arg16/Arg16) of $\beta_2$-adrenergic receptors displayed a worsening of bronchial airflow under repeated salbutamol treatment while carriers of the Gly16/Gly16 allel improved. Although $\beta_2$-adrenoreceptors are not causally involved in the pathophysiology of asthma, they are the prime therapeutic targets for acute and intermittent treatment of asthma symptoms. These examples illustrate the important contribution of specific GPCR genotypes for asthma susceptibility or therapy.

The observation of enhanced NPS-induced second messenger responses at NPSR $Ile^{107}$ could also have important consequences for brain function since the predominant sites of NPSR expression are found in the central nervous system. It might be possible that the $Ile^{107}$ isoform of NPSR is associated with changes in behavior or neuronal processing. In summary, we provide evidence that a naturally occurring polymorphism in the NPSR is producing a gain-of-function, resulting in enhanced second messenger signaling that could influence bronchial contractility and tissue remodeling. This polymorphism has been associated with an increased risk of asthma and our present pharmacological data may offer a functional explanation how the mutated NPSR protein could contribute to pathophysiological changes in asthma.

In some embodiments of the invention, exogenous NPSR agonist (e.g., a preparation comprising isolated NPS) or NPSR antagonist (e.g., a preparation comprising a compound of General Formula I above) may be administered to a human or animal subject to bring about a desired treatment or effect. In other embodiments of the invention, pharmacologic, electrical, radiofrequency, photonic or other means may be used to cause the subject's body to synthesize or retain increased or elevated amounts of a naturally occurring NPSR agonist or NPSR antagonist to bring about a desired treatment or effect. For example, in some applications, a stimulator or one or more electrodes may be implanted or positioned in the LC and used to stimulate the production of endogenous NPS by the LC, thereby augmenting the amounts of NPS that would naturally be present in the subject's body without such stimulation of the LC.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

What is claimed is:

1. A method for treating narcolepsy, hypersomnia, or anxiety in a human subject who suffers from such disorder, said method comprising the step of:
   A. administering an NPSR agonist to the subject in an amount and by a route of administration that is effective to treat said disorder;
   wherein the NPSR agonist comprises NPS or isolated NPS.

2. A method according to claim 1 wherein the NPSR agonist comprises isolated NPS.

3. A method according to claim 1 wherein the NPSR agonist comprises NPS which comprises the amino acid sequence Ser-Phe-Arg-Asn-Gly-Val-Gly-Thr-Gly-Met-Lys-Lys-Thr-Ser-Phe-Gln-Arg-Ala-Lys-Ser-OH (SEQ ID NO:1).

* * * * *

SEQUENCE LISTING

```
<160> NUMBER OF SEQ ID NOS: 27

<210> SEQ ID NO 1
<211> LENGTH: 20
<212> TYPE: PRT
<213> ORGANISM: Homo sapiens

<400> SEQUENCE: 1

Ser Phe Arg Asn Gly Val Gly Thr Gly Met Lys Lys Thr Ser Phe Gln
1               5                   10                  15

Arg Ala Lys Ser
            20

<210> SEQ ID NO 2
<211> LENGTH: 20
```

```
<212> TYPE: PRT
<213> ORGANISM: Pan troglodytes

<400> SEQUENCE: 2

Ser Phe Arg Asn Gly Val Gly Thr Gly Met Lys Lys Thr Ser Phe Arg
1               5                   10                  15

Arg Ala Lys Ser
            20

<210> SEQ ID NO 3
<211> LENGTH: 20
<212> TYPE: PRT
<213> ORGANISM: Mus musculus

<400> SEQUENCE: 3

Ser Phe Arg Asn Gly Val Gly Ser Gly Ala Lys Lys Thr Ser Phe Arg
1               5                   10                  15

Arg Ala Lys Gln
            20

<210> SEQ ID NO 4
<211> LENGTH: 20
<212> TYPE: PRT
<213> ORGANISM: Rattus sp.

<400> SEQUENCE: 4

Ser Phe Arg Asn Gly Val Gly Ser Gly Val Lys Lys Thr Ser Phe Arg
1               5                   10                  15

Arg Ala Lys Gln
            20

<210> SEQ ID NO 5
<211> LENGTH: 20
<212> TYPE: PRT
<213> ORGANISM: Canis lupus familiaris

<400> SEQUENCE: 5

Ser Phe Arg Asn Gly Val Gly Thr Gly Met Lys Lys Thr Ser Phe Arg
1               5                   10                  15

Arg Ala Lys Ser
            20

<210> SEQ ID NO 6
<211> LENGTH: 20
<212> TYPE: PRT
<213> ORGANISM: Gallus gallus

<400> SEQUENCE: 6

Ser Phe Arg Asn Gly Val Gly Ser Gly Ile Lys Lys Thr Ser Phe Arg
1               5                   10                  15

Arg Ala Lys Ser
            20

<210> SEQ ID NO 7
<211> LENGTH: 18
<212> TYPE: PRT
<213> ORGANISM: Homo sapiens

<400> SEQUENCE: 7

Ser Phe Arg Asn Gly Val Gly Thr Gly Met Lys Lys Thr Ser Phe Gln
1               5                   10                  15

Arg Ala
```

<210> SEQ ID NO 8
<211> LENGTH: 12
<212> TYPE: PRT
<213> ORGANISM: Homo sapiens

<400> SEQUENCE: 8

Ser Phe Arg Asn Gly Val Gly Thr Gly Met Lys Lys
1               5                   10

<210> SEQ ID NO 9
<211> LENGTH: 10
<212> TYPE: PRT
<213> ORGANISM: Rattus sp.

<400> SEQUENCE: 9

Ser Phe Arg Asn Gly Val Gly Ser Gly Val
1               5                   10

<210> SEQ ID NO 10
<211> LENGTH: 17
<212> TYPE: PRT
<213> ORGANISM: Homo sapiens

<400> SEQUENCE: 10

Asn Gly Val Gly Thr Gly Met Lys Lys Thr Ser Phe Gln Arg Ala Lys
1               5                   10                  15

Ser

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aggagcaagg acagtgaggc tcaa                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgcccaagca ggtgacaagg acct                                          24

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atactcgagc catgccagcc aacttcacag agggca                             36

<210> SEQ ID NO 14
<211> LENGTH: 36
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 14
gcttctagag ctcagcctag cactggcact gcccta                         36

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cagattttgg gaagtcca                                             18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agattaattc cccgagtc                                             18

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtttctagaa atgattagct cagtaaaact caa                            33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcagaattcg tcatgatttt gctctttgaa agg                            33

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgcagggagc aaagatcaca                                           20

<210> SEQ ID NO 20
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 20
aatctgcatc tcatgcctct ca                                              22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgtcgctgtc cacaatgcat                                                 20

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aatcagattt tccagacacc ttagaag                                         27

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cacggcatcg tcaccaact                                                  19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agccacacgc agctcattg                                                  19

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atctctttcc cctgcagggt catccgtctc c                                    31

<210> SEQ ID NO 26
<211> LENGTH: 25
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 26
tttctagaga gctgtcacct tggaa                                              25

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atactcgagc catgccagcc aacttcacag agggca                                  36
```